US012230388B2

(12) United States Patent
Makino

(10) Patent No.: US 12,230,388 B2
(45) Date of Patent: Feb. 18, 2025

(54) SERVER APPARATUS, NETWORK SYSTEM, INFORMATION PROVISION METHOD, AND RECORDING MEDIUM

(71) Applicant: OLYMPUS CORPORATION, Hachioji (JP)

(72) Inventor: Yuta Makino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 166 days.

(21) Appl. No.: 17/902,468

(22) Filed: Sep. 2, 2022

(65) Prior Publication Data
US 2022/0415497 A1    Dec. 29, 2022

Related U.S. Application Data

(63) Continuation of application No. PCT/JP2020/009845, filed on Mar. 6, 2020.

(51) Int. Cl.
*G16H 40/63* (2018.01)
*G16H 10/60* (2018.01)
*G16H 40/20* (2018.01)

(52) U.S. Cl.
CPC ............. *G16H 40/63* (2018.01); *G16H 10/60* (2018.01); *G16H 40/20* (2018.01)

(58) Field of Classification Search
CPC ......... G16H 40/63; G16H 10/60; G16H 40/20
See application file for complete search history.

(56) References Cited

U.S. PATENT DOCUMENTS 10,729,502 B1 *  8/2020  Wolf .................. G06V 20/49
11,380,437 B2 *  7/2022  Schermeier ............ G16H 10/60
(Continued)

FOREIGN PATENT DOCUMENTS

JP   2018-180797 A    11/2018
WO  WO-2018076112 A1 *  5/2018  ............. G06N 5/003

OTHER PUBLICATIONS

Jacobs et al., Nomenclature and databases for the surgical treatment of congenital cardiac disease—an updated primer and an analysis of opportunities for improvement, Dec. 2008, Cardiology in the Young, Cambridge, vol. 18, Iss. S2, pp. 38-62. ( Year: 2008).*

(Continued)

*Primary Examiner* — Christopher L Gilligan
(74) *Attorney, Agent, or Firm* — Oliff PLC

(57) ABSTRACT

A server apparatus communicates with a user terminal. The server apparatus includes a first storage area storing patient information and patient identification information, and a second storage area storing medical device identification information used for patient treatment, patient identification information on the patient that receives treatment by using the medical device, and status information indicating whether treatment is being provided. The server apparatus includes a processor that determines, when receiving a request command requesting the patient information that includes the medical device identification information, the patient identification information associated with the medical device identification information in which the status information indicates treatment is being provided, from among the patient identification information stored in the second storage area, and extracts and transmits the patient information associated with the determined patient identification information from among the patient identification information stored in the first storage area.

18 Claims, 19 Drawing Sheets

(56) References Cited

U.S. PATENT DOCUMENTS

| | | | |
|---|---|---|---|
| 12,040,074 B2* | 7/2024 | Rong | G06K 7/1417 |
| 2021/0050099 A1* | 2/2021 | Kirshenbaum | G16H 40/60 |
| 2024/0130776 A9* | 4/2024 | Maners | A61B 18/0218 |

OTHER PUBLICATIONS

Jul. 21, 2020 International Search Report issued in International Patent Application No. PCT/JP2020/009845.

* cited by examiner

| EXAMINATION ID | PATIENT ID | STATUS | DEVICE SN | |
|---|---|---|---|---|
| 11111111 | aaaaaaaa | EXAMINED | 1000 | ⟵ 1301 |
| 22222222 | bbbbbbbb | UNDER EXAMINATION | 1000 | |
| 33333333 | cccccccc | UNDER EXAMINATION | 2000 | |
| 44444444 | dddddddd | DISTRIBUTED | 1000 | |
| 55555555 | eeeeeeee | UNEXAMINED | | |
| ⋮ | ⋮ | ⋮ | ⋮ | |

13

| PATIENT ID | NAME | GENDER | AGE | BLOOD TYPE | ... |
|---|---|---|---|---|---|
| aaaaaaaa | AAA AAA | MALE | YA | A | ... |
| bbbbbbbb | BBB BBB | MALE | YB | B | ... |
| cccccccc | CCC CCC | FEMALE | YC | O | ... |
| ⋮ | ⋮ | ⋮ | ⋮ | ⋮ | |

10  1001

| PATIENT ID | EXAMINATION DATE | EXAMINATION TYPE | EXAMINATION RESULT | ... |
|---|---|---|---|---|
| | ⋮ | ⋮ | ⋮ | |
| bbbbbbbb | 2016/07/09 | EXAMINATION A | file009 | ... |
| | 2016/07/10 | EXAMINATION B | file010 | ... |
| | ⋮ | ⋮ | ⋮ | |

11  1101

| DEVICE ID | DEVICE SN | ADDRESS |
|---|---|---|
| 00001 | 1000 | ADD1 |
| 00002 | 2000 | ADD2 |
| ⋮ | ⋮ | ⋮ |

SERVER APPARATUS, NETWORK SYSTEM, INFORMATION PROVISION METHOD, AND RECORDING MEDIUM

CROSS-REFERENCE TO RELATED APPLICATION

This application is based upon and claims the benefit of priority to PCT Application No. PCT/JP2020/009845 filed on Mar. 6, 2020, the entire contents of which are incorporated herein by reference.

FIELD

The embodiments discussed herein are related to a server apparatus, a network system, an information provision method, and a recording medium.

BACKGROUND

An in-hospital network constructed in a medical institution, such as a hospital, can accumulate medical information including patient information in a server apparatus connected to the in-hospital network and centrally manage the information. The in-hospital network allows a plurality of staff members of the medical institution (for example, doctors, nurses, and the like) to share the medical information. The staff members of the medical institution in which the in-hospital network is constructed can read the medical information including the patient information accumulated in the server apparatus by using a predetermined user terminal (client) connected to the in-hospital network. The in-hospital network includes a network system constructed as a WEB system, and a general-purpose communication protocol such as, for example, the HTTP protocol is used for communication between the user terminal and the server apparatus in this type of in-hospital network.

When the medical information is read with the user terminal connected to the in-hospital network, a request command including information for determining the medical information to be read is transmitted from a communication terminal to the server apparatus. For example, information for identifying a patient is used as information for determining the medical information, and the information for identifying a patient is one of personal information. Therefore, the in-hospital network that transmits the request command including personal information from the communication terminal to the server apparatus is required to have a high level of security to prevent leakage of personal information.

SUMMARY

According to an aspect of the embodiment, a server apparatus that communicates with a user terminal includes: a memory including: a first storage area that stores patient information that includes personal information of a patient, and patient identification information for identifying the patient, the patient information and the patient identification information are stored in association with each other; and a second storage area that stores, in association with each other, (i) identification information on a medical device used for treatment on the patient, (ii) the patient identification information on the patient that receives the treatment by using the medical device, and (iii) status information indicating whether the treatment is being provided. A processor of the server apparatus is configured to: receive, from the user terminal, a request command requesting the patient information that includes the identification information on the medical device indicated in the request command; determine, among the patient identification information stored in the second storage area, patient identification information that is associated with the identification information on the medical device included in the received request command and in which the status information indicates the treatment is being provided; determine the patient information associated with the determined patient identification information from among the patient identification information stored in the first storage area; and transmit the determined patient information to the user terminal.

The object and advantages of the embodiment will be realized and attained by means of the elements and combinations particularly pointed out in the claims.

It is to be understood that both the foregoing general description and the following detailed description are exemplary and explanatory and are not restrictive of the embodiment.

BRIEF DESCRIPTION OF DRAWINGS

FIG. 2 is a diagram for describing one example of patient information, examination information, device information, and examination order stored in a storage unit of a server apparatus;

DESCRIPTION OF EMBODIMENTS

A security level of the in-hospital network described above differs for each in-hospital network depending on the difference in the scale, management system, and the like of the in-hospital network. For this reason, the in-hospital network may be operating in a state where the security level is not sufficiently high. In such an in-hospital network where the security level is not sufficiently high, when a request command including personal information is transmitted from a user terminal to a server apparatus, there is a high risk of leakage of the personal information included in the request command. Several embodiments about a server apparatus, a network system, an information provision method, and a recording medium that can reduce the leakage risk of patient personal information in the in-hospital network will be described below with reference to the drawings. Note that in the following description, detailed description on the well-known configuration, function, and processing in the in-hospital network that is an example of the network system will be omitted.

Figure 1:
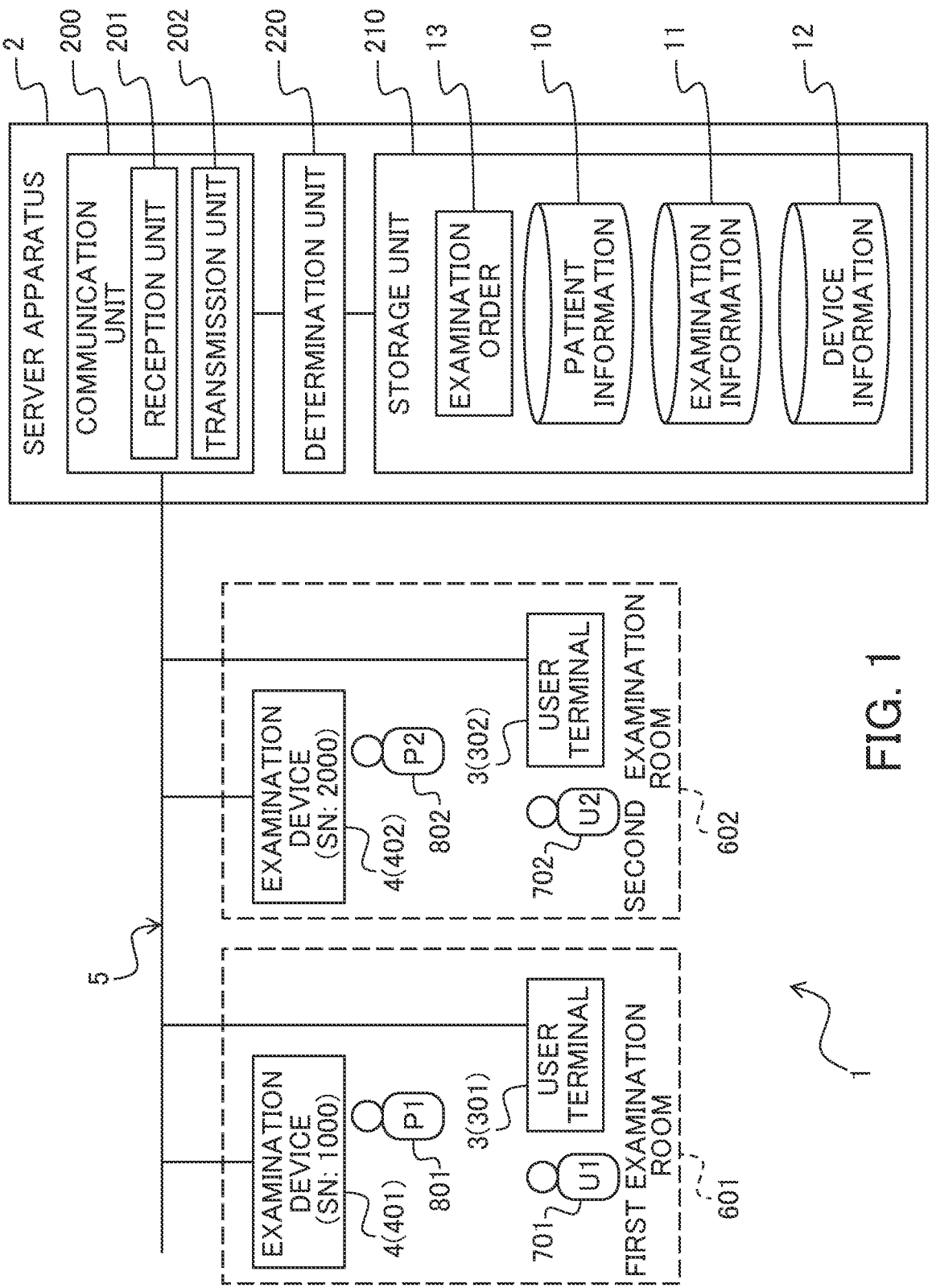
FIG. 1 is a diagram for describing an in-hospital network according to one embodiment.

FIG. 1 is a diagram for describing an in-hospital network according to one embodiment. The in-hospital network 1 illustrated in FIG. 1 includes a server apparatus 2, user terminals 3 (301 and 302) as clients, and examination devices 4 (401 and 402). In the following description, when the two user terminals 301 and 302 illustrated in FIG. 1 are not distinguished, the user terminals are described as user terminals 3. In the following description, when the two user terminals 301 and 302 are distinguished, the two user terminals 301 and 302 are described as a first user terminal 301 and a second user terminal 302, respectively. In the following description, when the two examination devices 401 and 402 illustrated in FIG. 1 are not distinguished, the examination devices are described as examination devices 4. In the following description, when the two examination devices 401 and 402 are distinguished, the two examination devices 401 and 402 are described as a first examination device 401 and a second examination device 402, respectively. Note that the in-hospital network 1 illustrated in FIG. 1 includes two user terminals 3 and two examination devices 4, but the number of user terminals 3 and the number of examination devices 4 in the in-hospital network 1 according to the present embodiment are arbitrary. In the in-hospital network 1, the number of user terminals 3 and the number of examination devices 4 may differ from each other.

The user terminal 3 in the present embodiment is an information processing apparatus managed to allow the use by a specific staff member of a medical facility where the in-hospital network 1 is constructed (for example, medical professionals such as doctors, nurses, and clinical examination technicians). The user terminal 3 is, for example, a communicable information processing apparatus such as a tablet computer, a desktop computer, and a notebook computer. The examination device 4 is a communicable electronic device to be used for examining patients. The plurality of examination devices including the first examination device 401 and the second examination device 402 includes, for example, an examination device to be used for endoscopic examinations, an examination device to be used for computed tomography (CT) examinations and magnetic resonance imaging (MRI) examinations, and the like. The examination device 4 is one example of medical devices in the in-hospital network 1.

The server apparatus 2, the user terminals 3, and the examination devices 4 are connected to each other via a transmission channel 5. The server apparatus 2, the user terminals 3, and the examination devices 4 are each connected to the transmission channel 5, for example, by a communication cable such as a local area network (LAN) cable. One or more of the server apparatus 2, the user terminals 3, and the examination devices 4 may be connected to the transmission channel 5, for example, by performing wireless communication with a wireless access point (not shown) connected to the transmission channel 5.

Alternatively, the user terminal 3 may be connected to the examination device 4 without going through the transmission channel 5. The user terminal 3 connected to the examination device 4 without going through the transmission channel 5 may, for example, communicate with the server apparatus 2 via the examination device 4 and the transmission channel 5.

The server apparatus 2 is an information processing apparatus that accumulates and centrally manages medical information including patient identification information. The server apparatus 2 includes a communication unit 200, a storage unit 210, and a determination unit 220.

The communication unit 200 communicates with the user terminal 3, the examination device 4, and the like via the transmission channel 5. The communication unit 200 includes a reception unit 201 and a transmission unit 202. The reception unit 201 receives various data transmitted from the user terminal 3, the examination device 4, and the like to the server apparatus 2 via the transmission channel 5. The data received by the reception unit 201 includes a request command (request) for patient information and the like from the user terminal 3, and examination data from the examination device 4. The transmission unit 202 transmits various data to be transmitted to the user terminal 3, the examination device 4, and the like via the transmission channel 5. The data transmitted by the transmission unit 202 includes a response to the request command from the user terminal 3, and information on the examination for the examination device 4 (for example, information for identifying a patient on which the examination is performed by the examination device 4).

The communication unit 200 of the server apparatus 2 in the in-hospital network 1 of the present embodiment can perform communication according to an original communication protocol in the in-hospital network 1 and communication according to the hypertext transfer protocol (HTTP). For example, the user terminal 3 can transmit an HTTP request requesting the patient information to the server apparatus 2, and the server apparatus 2 can transmit the requested patient information as a response to the HTTP request (HTTP response) to the user terminal 3. Therefore, a user of the user terminal 3 can read various pieces of information such as the patient information and the like stored (housed) in the storage unit 210 of the server apparatus 2, on the web browser running in the user terminal 3. For example, when a doctor 701 examines a patient 801 in a first examination room 601 where the first examination device 401 is installed, the doctor 701 can read the patient information on the patient 801 and the like by using the first user terminal 301. Similarly, when a doctor 702 examines a patient 802 in a second examination room 602 where the second examination device 402 is installed, the doctor 702 can read the patient information on the patient 802 and the like by using the second user terminal 302.

The storage unit 210 of the server apparatus 2 stores various pieces of information. The storage unit 210 includes a patient information storage area 10, an examination information storage area 11, a device information storage area 12, and an examination order storage area 13. For example, the patient information, examination information, device information, and order information as illustrated in FIG. 2 are stored (housed) in the patient information storage area 10, the examination information storage area 11, the device information storage area 12, and the examination order storage area 13, respectively.

FIG. 2 is a diagram for describing one example of the patient information, the examination information, the device information, and the examination order stored in the storage unit of the server apparatus.

The patient information stored in the patient information storage area 10 includes various pieces of information on the patient, including, for example, the patient's name, gender, age, and blood type. The patient information is stored (housed) in the patient information storage area 10 in association with a patient ID, which is patient identification information for identifying the patient. The examination information stored in the examination information storage area 11 includes information on the examination the patient has undergone, for example, the examination date, examination type, and examination result (examination data), findings, and the like. The examination information is stored in the examination information storage area 11 for each patient in association with the patient ID. The device information stored in the device information storage area 12 includes device identification information for identifying the examination device connected to the in-hospital network 1, for example, the serial number (SN) of the device and the address of the examination device in the in-hospital network 1. The order information stored in the examination order storage area 13 includes, for example, information on the examination performed during a specific period (for example, one day) at the medical facility where the in-hospital network 1 is constructed, and management of examination data. The order information includes, for example, the patient ID of the patient who undergoes the examination, status information indicating the progress of the examination (status), and the SN of the device. In the status information in the examination order storage area 13 illustrated in FIG. 2, "examined" indicates that the examination has been finished, and "under examination" indicates that the examination is currently being performed. Meanwhile, in the status information in the examination order storage area 13 illustrated in FIG. 2, "distributed" indicates that the examination data transmission to the examination device has been completed although before the examination (that is, this indicates that the examination device 4 to be used for examining the patient has been determined). "Unexamined" in the status information indicates before the examination and the examination data has not been transmitted to the examination device. The order information is stored in the examination order storage area 13 for each examination in association with examination identification information for identifying the examination, for example, the examination ID. In the following description, transmitting the examination data to the examination device to determine the examination device to be used for the examination is called "examination distribution (distribution of examination)", and completion of the distribution of examination is called "distributed".

The patient information storage area 10 is one example of a first storage area that stores, for each patient, the patient identification information and the patient information in association with each other. The examination order storage area 13 is one example of a second storage area that stores, for each examination, the device identification information on the examination device, the patient identification information on the patient who undergoes examination using the examination device, and the status information indicating the progress information of the examination in association with each other.

The storage unit 210 in the server apparatus 2 of the present embodiment is implemented by one or more storage apparatuses. The patient information storage area 10, the examination information storage area 11, the device information storage area 12, and the examination order storage area 13 may be provided in a single storage apparatus or may be provided in two or more storage apparatuses in a distributed manner.

The determination unit 220 of the server apparatus 2 illustrated in FIG. 1 determines and extracts information to be transmitted to the user terminal 3, the examination device 4, and the like as a response to the request command based on the request command received by the server apparatus 2.

In the in-hospital network 1 of the present embodiment, as described above, the HTTP request can be used as the request command requesting the patient information, the examination information, and the like to be transmitted from the user terminal 3 to the server apparatus 2. The target of request in the HTTP request is designated by a uniform resource locator (URL). When requesting for the patient information, the examination information, and the like by the HTTP request, the user terminal 3 according to the present embodiment designates the request target by the URL including a parameter indicating the requested information and a parameter indicating the device identification information for identifying the examination device (for example, device SN). That is, in the in-hospital network 1 of the present embodiment, when the patient information, the examination information, and the like are requested by the HTTP request, the request target is designated by the URL that does not include patient personal information (for example, patient ID and the like).

The determination unit 220 of the server apparatus 2 according to the present embodiment determines the patient ID based on the device SN described in the URL of the HTTP request and the order information in the examination order storage area 13. For example, when the device SN described in the URL is "1000", the determination unit 220 searches for order information 1301 in which the device SN is "1000" and the status information is "under examination" in the examination order storage area 13, as shown in FIG. 2. After that, the determination unit 220 searches for (determines) patient information 1001 in the patient information storage area 10 by using the patient ID of the searched order information 1301 as a search key, and extracts the patient information 1001 to be transmitted to the user terminal 3 that has sent the HTTP request.

For example, when transmitting, to the server apparatus 2, the HTTP request requesting the examination data on the examination the patient is currently undergoing, the user terminal 3 according to the present embodiment designates the request target by the URL in which the information indicating that the examination data is requested and the device SN are described. In this case as well, the determination unit 220 of the server apparatus 2 determines the patient ID, for example, based on the device SN described in the URL of the HTTP request and the order information in the examination order storage area 13. For example, when the device SN described in the URL is "1000", the determination unit 220 searches for order information 1301 in which the device SN is "1000" and the status information is "under examination" in the examination order storage area 13, as shown in FIG. 2. After that, the determination unit 220 searches for examination information 1101 in the examination information storage area 11 by using the patient ID of the searched order information 1301 as a search key, and for example, determines and extracts the examination information to be transmitted to the user terminal 3 that has sent the HTTP request based on information on the examination date.

The determination unit 220 of the server apparatus 2 according to the present embodiment searches for device information 1201 in the device information storage area 12, for example, based on a parameter in the URL of the HTTP request or the device SN in the order information within the examination order storage area 13. In this case, based on the searched device information 1201, the determination unit 220 determines and extracts the address of the examination device 4 that transmits information such as the patient ID of the patient who undergoes the examination.

Figure 3:
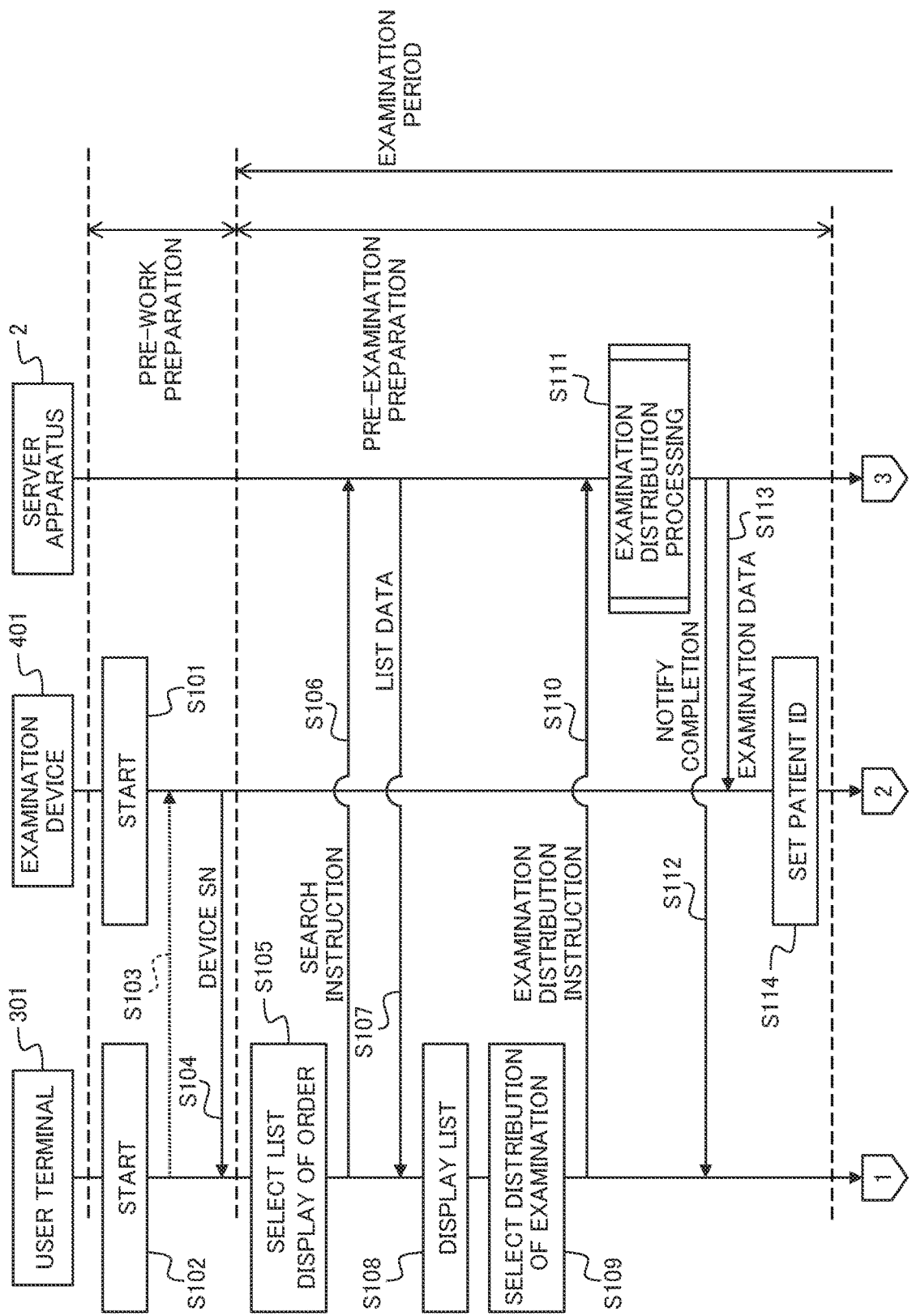
FIG. 3 is a sequence diagram (No. 1) for describing one example of processing to be performed in the in-hospital network according to one embodiment.
Figure 4:
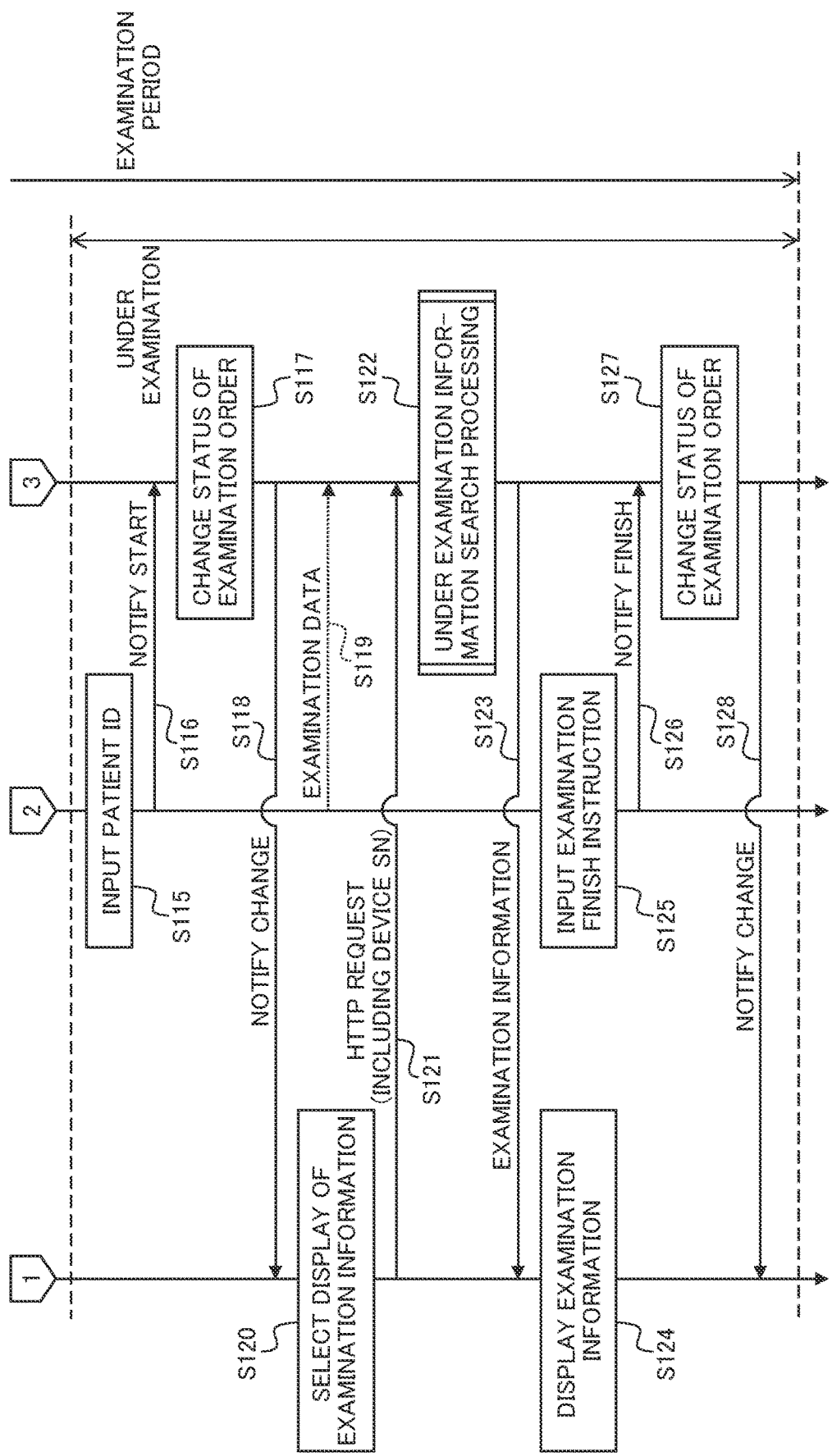
FIG. 4 is a sequence diagram (No. 2) for describing one example of processing to be performed in the in-hospital network according to one embodiment.

FIG. 3 is a sequence diagram (No. 1) for describing one example of processing to be performed in the in-hospital network according to one embodiment. FIG. 4 is a sequence diagram (No. 2) for describing one example of processing to be performed in the in-hospital network according to one embodiment. FIGS. 3 and 4 show one example of processing to be performed by the first examination device 401, the first user terminal 301, and the server apparatus 2 when a patient is examined by using the first examination device 401 installed in the first examination room 601. The first user terminal 301 is set, for example, to connect to the first examination device 401 in the in-hospital network 1 associated in advance when startup is complete or at the time of logging in.

In the in-hospital network 1, to begin with, pre-work preparation including steps S101 to S104 illustrated in FIG. 3 is performed. In the pre-work preparation, the first examination device 401 is started (step S101), and the first user terminal 301 is started (step S102). When the startup of the first user terminal 301 is completed, the first user terminal 301 notifies the first examination device 401 that the startup is completed (step S103). The first examination device 401 that has received the notification transmits the serial number (SN) of the first examination device 401 to the first user terminal 301 as device identification information for identifying the examination device (step S104).

When the pre-work preparation (steps S101 to S104) is finished, in the in-hospital network 1, pre-examination preparation including steps S105 to S114 is performed. Although omitted in FIG. 3, in the pre-examination preparation, to begin with, the Web browser is started in the first user terminal 301 to display a predetermined menu screen on the display apparatus of the first user terminal 301. The menu screen includes, for example, a button to select processing on the examination order, a button to select reading the patient information, and a button to select reading the examination information.

When the user of the first user terminal 301 (doctor 701) operates the first user terminal 301 and selects list display of the examination order (step S105), the first user terminal 301 transmits the search instruction for the examination order to the server apparatus 2 (step S106). The server apparatus 2 that has received the search instruction reads the order information in the examination order storage area 13 of the storage unit 210 based on the search instruction, and transmits list data of the read order information to the first user terminal 301 (step S107). The first user terminal 301 that has received the list data displays the received list data (step S108). The list data displayed on the first user terminal 301 includes the patient ID of the patient who undergoes the examination and the status information. Display of the list data may allow, for example, distribution of the examination, or display of the examination data of examination currently performed or the examination data of examination performed in the past.

After the list data is displayed, when the doctor 701 operates the first user terminal 301 and selects the distribution of examination on one patient (step S109), the first user terminal 301 transmits an examination distribution instruction to the server apparatus 2 (step S110). The examination distribution instruction includes information for instructing the first examination device 401 associated with the first user terminal 301 to perform the selected examination on the patient. The server apparatus 2 that has received the examination distribution instruction performs examination distribution processing based on the examination distribution instruction (step S111). A specific example of the examination distribution processing to be performed by the server apparatus 2 (step S111) will be described later with reference to FIG. 5. When the examination distribution processing is finished, the server apparatus 2 transmits a completion notification of the examination distribution to the first user terminal 301 (step S112), and transmits the examination data to the first examination device 401 (step S113). Although omitted in FIG. 3, the first user terminal 301 that has received the completion notification changes the status information on the examination for which the examination distribution in the displayed list data is completed to a value indicating that the examination distribution is completed. The examination data to be transmitted to the first examination device 401 includes, for example, the patient ID, and the first examination device 401 that has received the examination data reads and sets the patient ID included in the examination data (step S114).

The pre-examination preparation is performed for each examination identified with the order information stored in the examination order storage area 13, in other words, the examination identification information. The doctor 701 who performs the examination using the first examination device 401 selects the examination distribution in step S109 for the examination of which the doctor 701 is in charge, out of the examination order included in the displayed list data. The communication performed between the first user terminal 301 and the server apparatus 2 in steps S110 and S112 is performed by the HTTP request and HTTP response as described later. Note that the communication performed between the first user terminal 301 and the server apparatus 2 in steps S110 and S112 may be performed, for example, according to the original communication protocol in the in-hospital network 1. When the communication in step S110 is performed according to the original communication protocol, the examination distribution instruction may include the patient identification information for identifying the patient who undergoes the examination (patient ID), and the device identification information for identifying the first examination device 401 used for the examination (device SN).

When the time has come to perform the examination of which the examination distribution is completed by the pre-examination preparation illustrated in FIG. 3 and it becomes possible to start the examination, for example, processing under examination including steps S115 to S128 illustrated in FIG. 4 is performed in the in-hospital network 1. In the processing under examination, to begin with, the patient ID is input to the first examination device 401 by the doctor 701 (step S115), and the first examination device 401 notifies the server apparatus 2 of the start of the examination (step S116). The notification of examination start includes, for example, the patient ID input in step S115. The server apparatus 2 that has received the notification of examination start changes the status information of the examination order based on the patient ID included in the notification (step S117), and notifies the first user terminal 301 of the status change (step S118). After the notification of examination start, the examination data is transmitted from the first examination device 401 to the server apparatus 2 (step S119).

In step S117, the server apparatus 2 searches for the order information (examination order) including the patient ID read from the examination start notification in the examination order storage area 13. After that, the server apparatus 2 changes the status information in the order information from a value indicating that the examination has been distributed to a value indicating that the examination is currently being performed. In step S118, the server apparatus 2 reflects the change in the status information in step S117 in the first user terminal 301. The communication performed between the first examination device 401 and the server apparatus 2 in steps S116 and S119 is performed, for example, according to the original communication protocol in the in-hospital network 1.

After starting the examination, the examination data acquired by the first examination device 401 in the examination currently performed and accumulated in the server apparatus 2 can be read on the first user terminal 301. Therefore, when the display of the examination information is selected on the first user terminal 301 by the operation of the doctor 701 (step S120), the first user terminal 301 generates the HTTP request requesting the examination information on the examination currently performed (examination data) and transmits the HTTP request to the server apparatus 2 (step S121). The URL designating the request target in the HTTP request transmitted to the server apparatus 2 in step S121 does not include the patient personal information such as the patient ID as described above.

Based on the HTTP request, the server apparatus 2 that has received the HTTP request performs under examination information search processing for searching for the examination data acquired by the first examination device 401 in the examination current performed and accumulated in the server apparatus 2 (step S122). The processing of step S122 is performed by the determination unit 220 of the server apparatus 2. A specific example of the under examination information search processing (step S122) will be described later with reference to FIG. 6. When the under examination information search processing is finished, the server apparatus 2 transmits the searched examination information as an HTTP response to the first user terminal 301 (step S123), and the first user terminal 301 displays the received examination information (step S124). Step S123 may be repeated, for example, until the examination is finished, or until the display of the examination information is finished in the first user terminal 301. Step S124 is performed every time the examination information from the server apparatus 2 is received.

When the examination on the patient to whom the patient ID input in step S115 is assigned is finished and the doctor 701 inputs an examination finish instruction to the first examination device 401 (step S125), the first examination device 401 notifies the server apparatus 2 of the examination finish (step S126). The notification of examination finish includes, for example, the patient ID input in step S115. The server apparatus 2 that has received the notification of examination finish changes the status information of the examination order based on the patient ID included in the notification (step S127), and notifies the first user terminal 301 of the status change (step S128).

Figure 5:
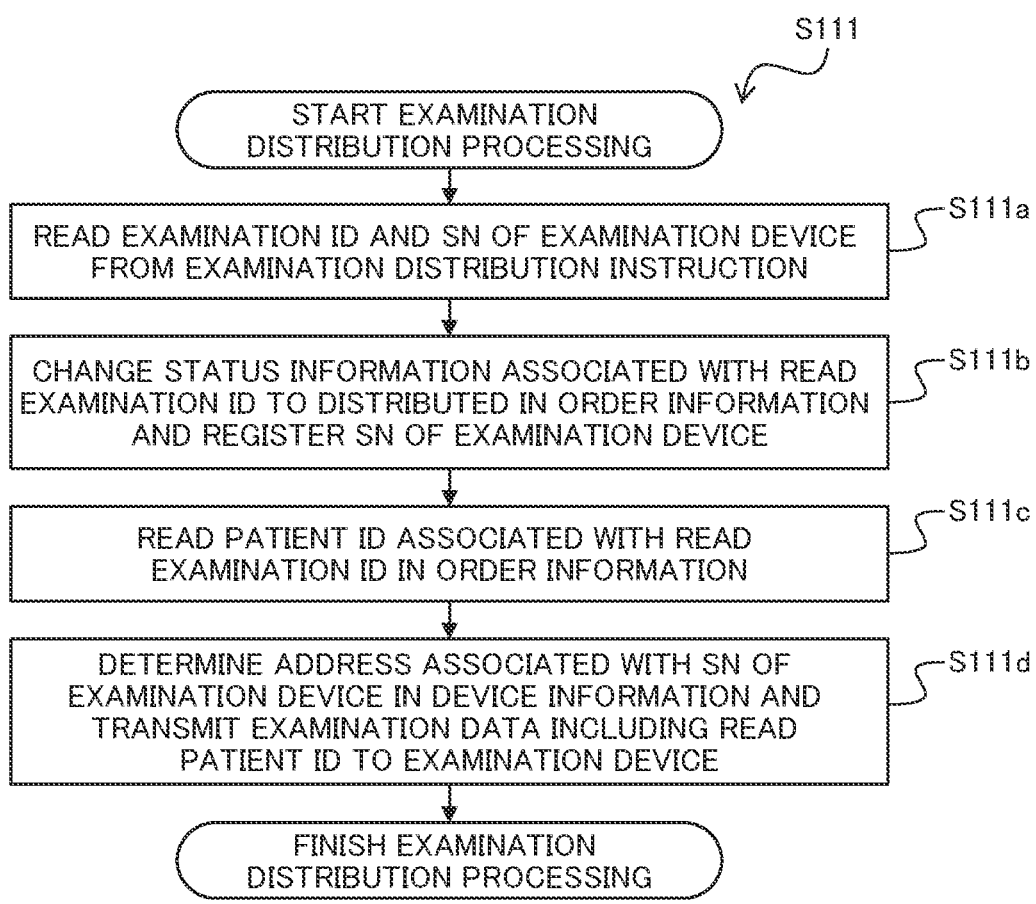
FIG. 5 is a flowchart for describing one example of distribution processing to be performed by the server apparatus.

FIG. 5 is a flowchart for describing one example of examination distribution processing to be performed by the server apparatus. FIG. 5 describes one example of details of the examination distribution processing performed by the server apparatus 2 (step S111) when the examination distribution instruction transmitted from the first user terminal 301 to the server apparatus 2 in the sequence illustrated in FIG. 3 is the HTTP request. In this case, the examination distribution instruction includes, for example, the examination ID and the SN of the device to use in the examination.

When the examination distribution processing starts, to begin with, the determination unit 220 of the server apparatus 2 reads the examination ID and the SN of the examination device from the examination distribution instruction (step S111*a*). Next, the determination unit 220 changes the status information associated with the examination ID read from the examination distribution instruction in the order information in the examination order storage area 13 to a value indicating that the examination distribution has been completed (distributed), and registers the SN of the examination device (step S111*b*). Next, the determination unit 220 reads the patient ID associated with the examination ID in the order information (step S111*c*). After that, the determination unit 220 determines the address associated with the device SN in the device information storage area 12 based on the SN of the examination device, and uses this address to transmit the examination data including the patient ID to the first examination device 401 (step S111*d*).

Figure 6:
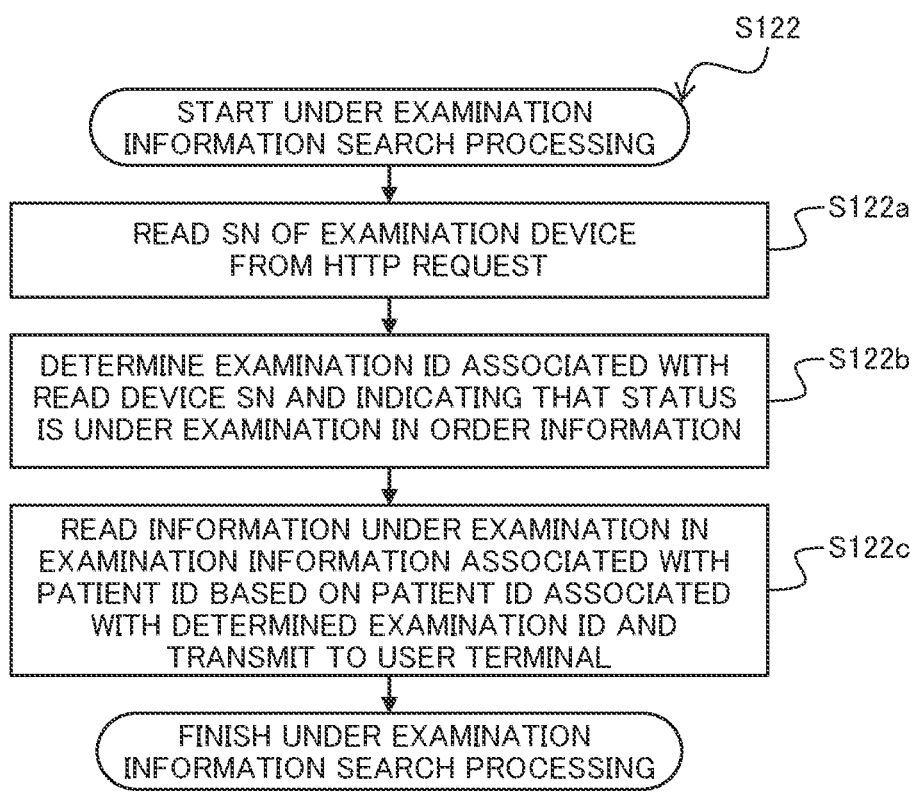
FIG. 6 is a flowchart for describing one example of under examination information search processing to be performed by the server apparatus.

FIG. 6 is a flowchart for describing one example of under examination information search processing to be performed by the server apparatus. FIG. 6 describes one example of details of the under examination information search processing (step S122) to be performed by the server apparatus 2 when the HTTP request requesting display of the examination information is transmitted from the first user terminal 301 to the server apparatus 2 in the sequence illustrated in FIG. 4.

When the under examination information search processing starts, to begin with, the determination unit 220 of the server apparatus 2 reads the SN of the examination device from the HTTP request (step S122*a*). Next, the determination unit 220 determines the examination identification information (examination ID) that is information associated with the device SN read from the HTTP request and indicates that the status information is under examination from the order information in the examination order storage area 13 (step S122b). Next, the determination unit 220 reads information under examination in the examination information associated with the patient ID based on the patient ID associated with the determined examination identification information, and transmits the read information under examination to the first user terminal 301 (step S122c).

In the in-hospital network 1 of the present embodiment, when the examination distribution instruction or the examination information is requested by the HTTP request, as described above, instead of the personal information like the patient ID, the examination ID associated with the patient ID in the examination order or the device identification information for identifying the examination device is used. Therefore, it is possible to prevent the leakage of personal information when the request command such as the HTTP request according to a general-purpose communication protocol is transmitted from the first user terminal 301 to the server apparatus 2.

Next, with reference to FIGS. 7 to 11, a specific example of processing to be performed in the in-hospital network 1 and screen transition of the first user terminal 301 will be described.

Figure 7:
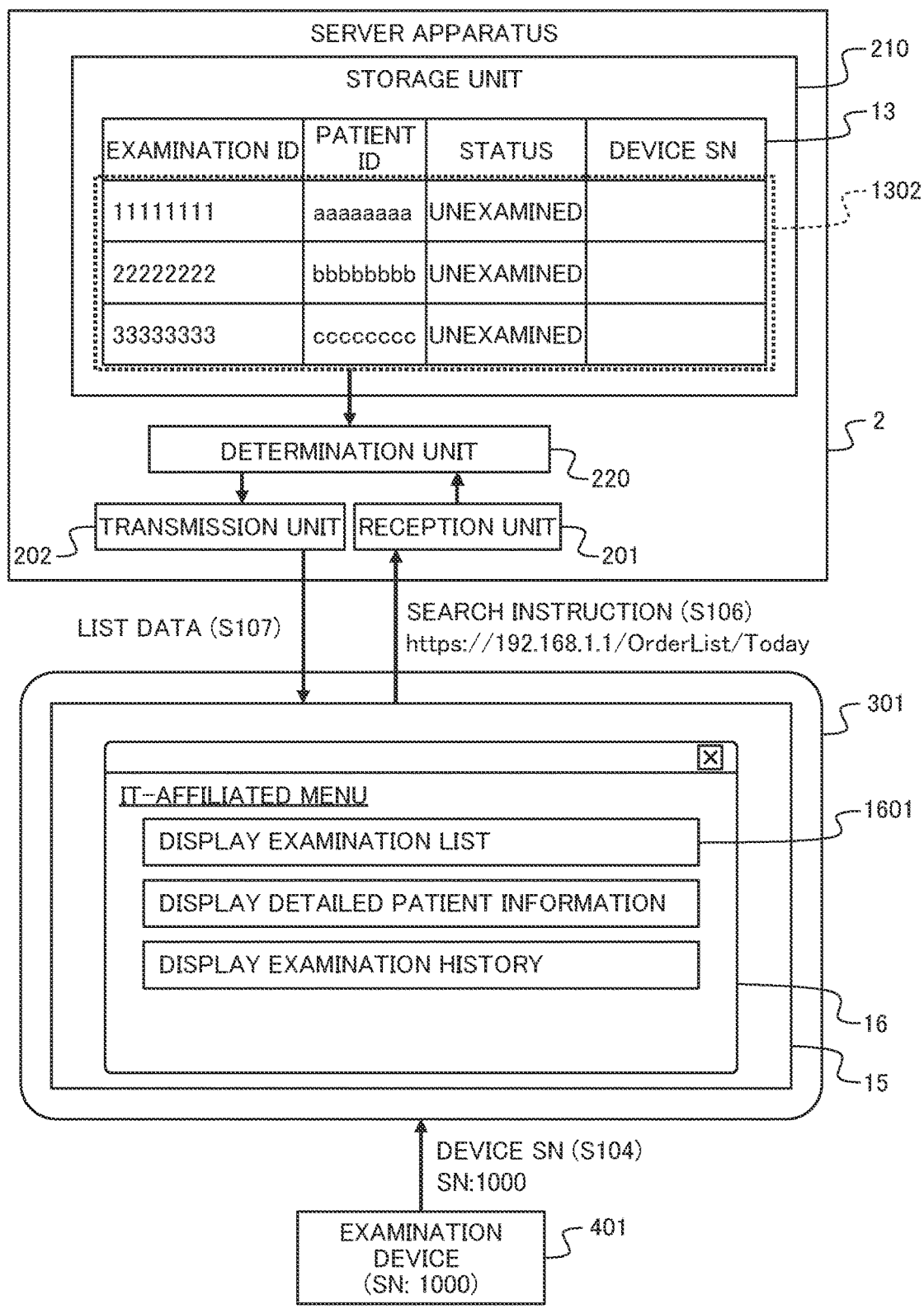
FIG. 7 is a diagram for describing a specific example of processing of displaying list data of the examination order on a first user terminal.
Figure 8:
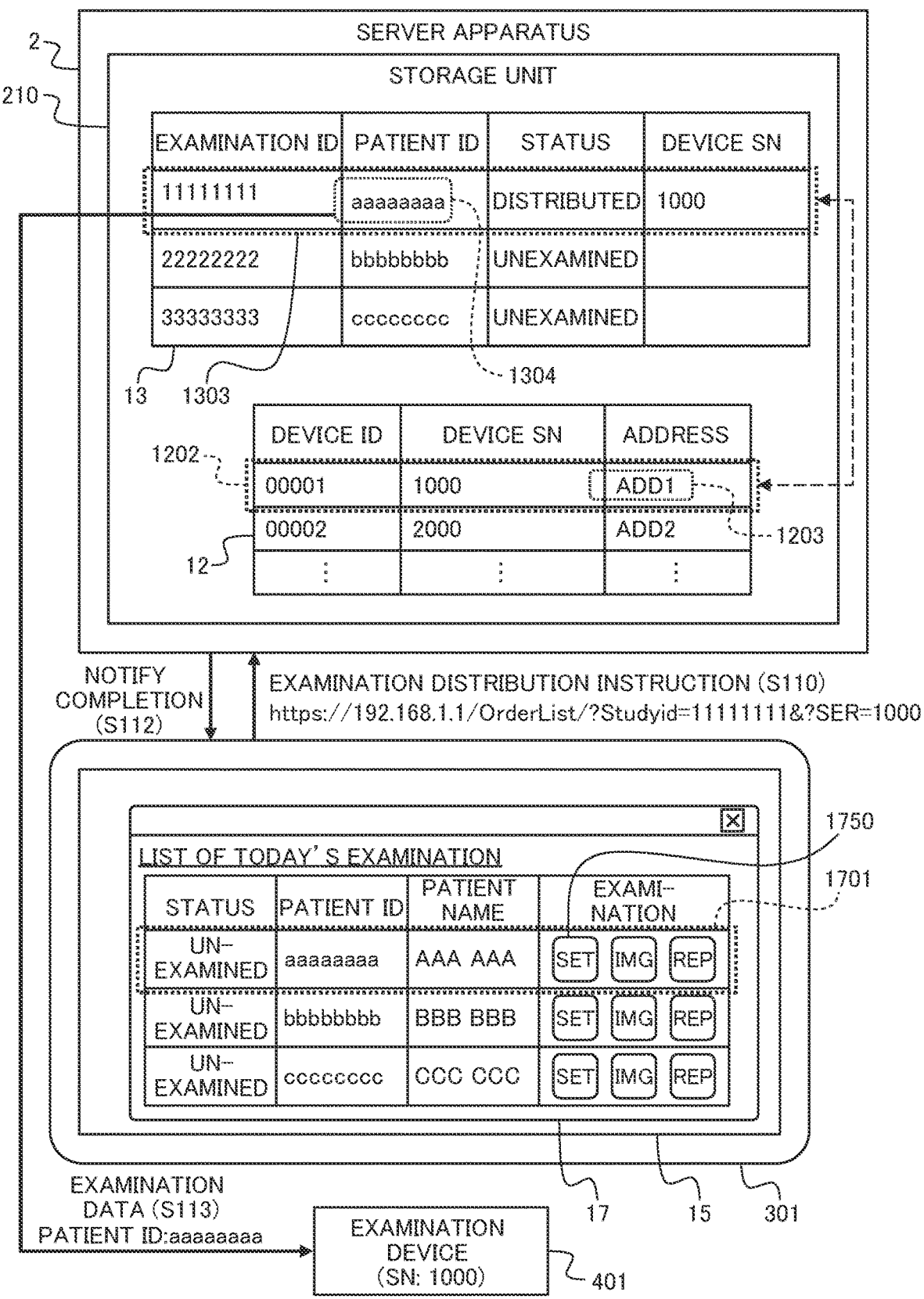
FIG. 8 is a diagram for describing a specific example of processing of distributing an examination by using the first user terminal.
Figure 9:
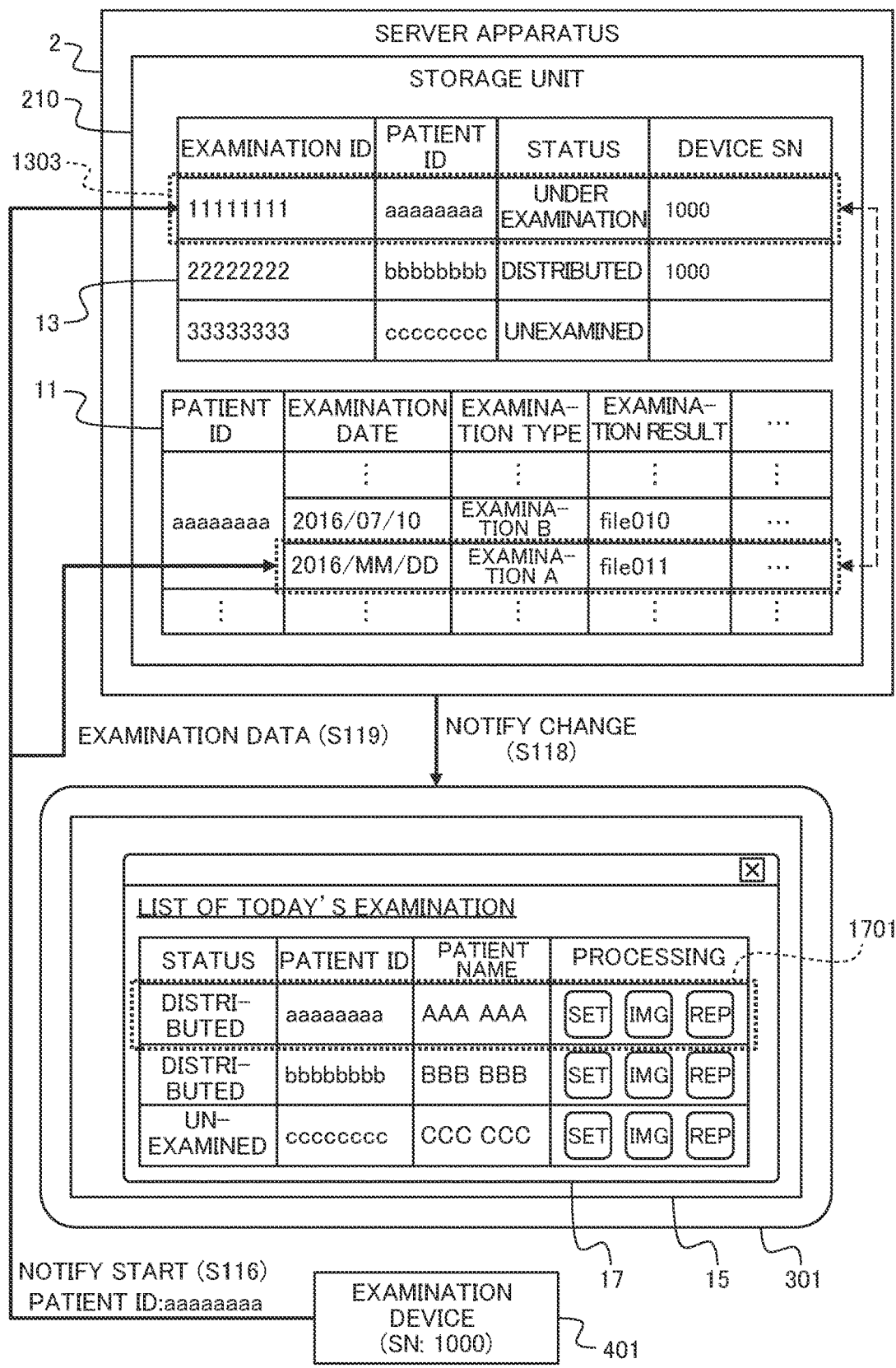
FIG. 9 is a diagram for describing a specific example of processing when the examination is started.
Figure 10:
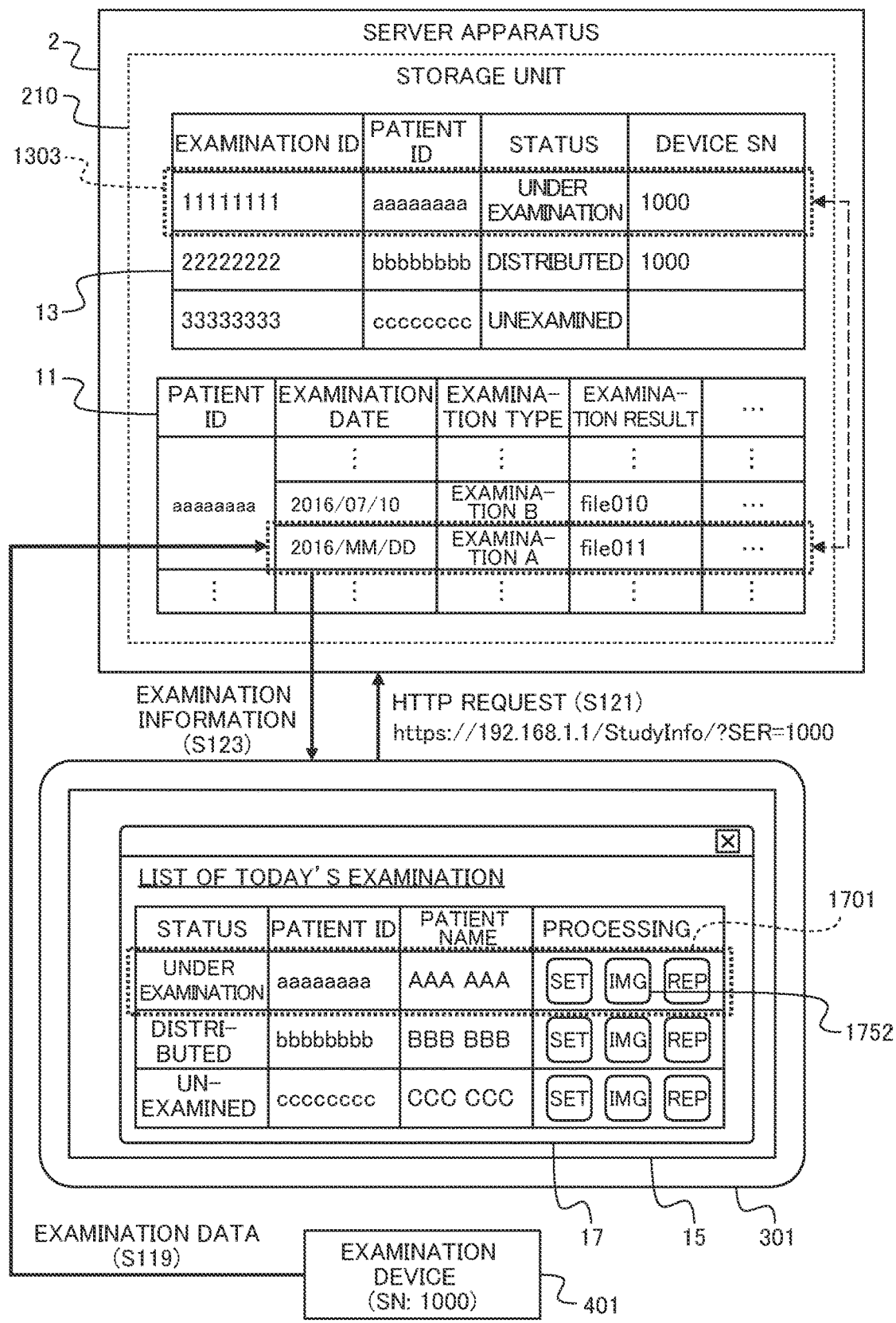
FIG. 10 is a diagram for describing a specific example of processing of displaying examination data during the examination.
Figure 11:
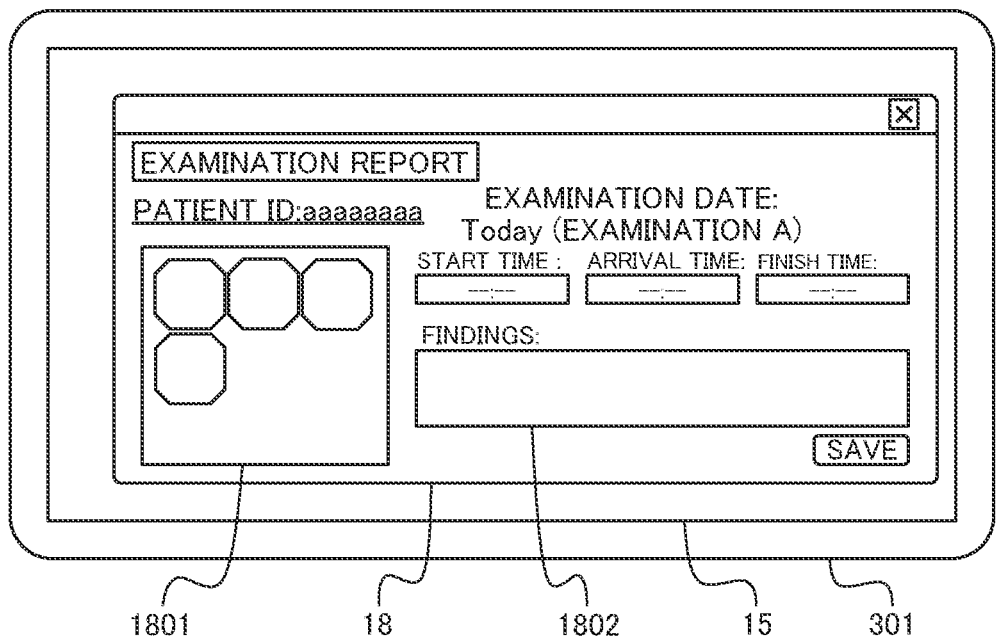
FIG. 11 is a diagram for describing a specific example of the examination data displayed on the first user terminal.

FIG. 7 is a diagram for describing a specific example of processing of displaying the list data of the examination order on the first user terminal. FIG. 8 is a diagram for describing a specific example of processing of distributing an examination by using the first user terminal. FIG. 9 is a diagram for describing a specific example of processing when the examination is started. FIG. 10 is a diagram for describing a specific example of processing of displaying the examination data during the examination. FIG. 11 is a diagram for describing a specific example of the examination data displayed on the first user terminal. Note that in each of FIGS. 8 to 10, the reception unit 201, the transmission unit 202, and the determination unit 220 of the server apparatus 2 are omitted.

In the in-hospital network 1 of the present embodiment, when the first examination device 401 and the first user terminal 301 are started, as illustrated in FIG. 7, the device SN that is the device identification information for identifying the examination device is transmitted from the first examination device 401 to the first user terminal 301 (step S104). A menu screen 16 that presents services available in the in-hospital network 1 is displayed on a display panel 15 of the started first user terminal 301. A button 1601 of "display examination list" in the menu screen 16 receives an operation input to display a list of examination order (order information) stored in the examination order storage area 13 of the storage unit 210 of the server apparatus 2. When the display panel 15 is a touch panel, by touching an area where the button 1601 is displayed on the display panel 15, an operation input into the button 1601 is performed. When the user (doctor 701) performs an operation of selecting the button 1601, the first user terminal 301 transmits the search instruction to the server apparatus 2 (step S106). The search instruction includes, for example, the URL (https://192.168.1.1/OrderList/Today) as illustrated in FIG. 7. "https://192.168.1.1/" in this URL is a parameter designating a domain. In this URL, "OrderList/" is a parameter indicating the list of the examination order, and "Today" is a parameter indicating a period to be included in the list. The search instruction is transmitted to the server apparatus 2 via the transmission channel 5 and received by the reception unit 201 of the server apparatus 2. The search instruction received by the reception unit 201 is transferred, for example, to the determination unit 220. Based on the parameter described in the URL included in the search instruction, the determination unit 220 determines and extracts order information 1302 on the examination that is performed on the day, out of the examination order stored in the examination order storage area 13 of the storage unit 210. The extracted order information is transferred to the transmission unit 202 and is transmitted from the server apparatus 2 to the first user terminal 301 as list data (step S107). Upon receiving the list data, the first user terminal 301 switches the display of the display panel 15, for example, to an examination list 17 as illustrated in FIG. 8.

The examination list 17 includes, for example, the status information on the examination to be performed on the day, patient ID, patient name, and processing button. "Unexamined" in the status information of the examination list 17 illustrated in FIG. 8 indicates that the examination distribution has not been performed and the examination has not been performed, as described above. The examination distribution is performed, for example, by the user of the first user terminal 301 (doctor 701) pressing a set button 1750 for the examination of which the status information in the examination list 17 is "unexamined". For example, when the "SET" button 1750 included in order information (examination order) 1701 in which the patient ID in the examination list 17 is "aaaaaaaa" is pressed, the first user terminal 301 transmits the examination distribution instruction for the examination the patient whose patient ID is "aaaaaaaa" undergoes to the server apparatus 2. The distribution instruction includes, for example, the URL (https://192.168.1.1/OrderList/?Studyid=11111111&?SER=1000) as illustrated in FIG. 8. "?Studyid=11111111&?SER=1000" in this URL is a parameter indicating the examination ID of the examination that is the target of the examination distribution and the SN of the examination device used for the examination. The examination ID is designated by "?Studyid=11111111", and the device SN is designated by "?SER=1000".

As illustrated in FIG. 8, out of the order information in the examination order storage area 13, the server apparatus 2 that has received the examination distribution instruction changes the status information in the order information 1303 in which the examination ID designated by the examination distribution instruction is "11111111" to "distributed", and sets the device SN to "1000" (step S111b). After that, the server apparatus 2 transmits the completion notification to the first user terminal 301 (step S112), and transmits the examination data to the first examination device 401 (steps S111d and S113). For example, based on the device SN set in the order information 1303, the server apparatus 2 searches for device information 1202 in which the device SN in the device information storage area 12 is "1000", and uses an address 1203 in the device information 1202 to transmit the examination data to the first examination device 401. The examination data to be transmitted to the first examination device 401 includes the patient ID 1304 in the order information 1303. With this configuration, the first examination device 401 is set to be used for the examination on the patient whose patient ID is "aaaaaaaa". Upon receiving the completion notification from the server apparatus 2, the first user terminal 301 updates the examination list 17 displayed on the display panel 15. In the updated examination list 17, for example, as illustrated in FIG. 9, the status information in the order information (examination order) 1701 in which the patient ID is "aaaaaaaa" is changed to "distributed". Although detailed description is omitted, by performing the similar operation on the order information (examination order) in which the patient ID is "bbbbbbbb", as in the examination list 17 illustrated in FIG. 9, the status information in the order information is changed to "distributed".

After performing the examination distribution on the examination the patient whose patient ID is "aaaaaaaa" undergoes, when the time has come to start the examination on the patient and the examination is ready, the doctor 701 inputs the patient ID in the first examination device 401 (step S115) and starts the examination. At this time, the first examination device 401 transmits the examination start notification including information indicating the patient ID of the patient who undergoes the examination to the server apparatus 2 as illustrated in FIG. 9, according to the original communication protocol in the in-hospital network 1 (step S116). Upon receiving the examination start notification, based on the patient ID included in the notification, out of the order information in the examination order storage area 13, the server apparatus 2 changes the status information on the order information 1303 for the patient whose patient ID is "aaaaaaaa" to "under examination", and transmits a change notification to the first user terminal 301 (step S118). Therefore, when the examination is started on the patient whose patient ID is "aaaaaaaa", in the order information 1701 for the patient whose patient ID in the examination list 17 displayed on the display panel 15 of the first user terminal 301 is "aaaaaaaa", the status information is changed to "under examination", for example, as in the order information 1701 in the examination list 17 illustrated in FIG. 10. When the examination is started on the patient whose patient ID is "aaaaaaaa", the first examination device 401 transmits the examination data to the server apparatus 2 (step S119). The server apparatus 2 stores (houses) the received examination data in the examination information storage area 11 as examination data on the patient whose patient ID is "aaaaaaaa".

When the examination is being performed on the patient whose patient ID is "aaaaaaaa", the doctor 701 can read the examination data obtained in the examination currently being performed by using the first user terminal 301. For example, in the examination list 17 displayed on the display panel 15 of the first user terminal 301 illustrated in FIG. 10, the order information 1701 on the patient whose patient ID is "aaaaaaaa" includes a button 1752 called "IMG". When this button 1752 called "IMG" is pressed, the first user terminal 301 transmits the HTTP request requesting the examination data of the examination currently performed on the patient whose patient ID is "aaaaaaaa" to the server apparatus 2. This HTTP request includes, for example, the URL (https://192.168.1.1/StudyInfo/?SER=1000) as illustrated in FIG. 10. In this URL, "StudyInfo/" is a parameter indicating the examination data, and "?SER=1000" is a parameter indicating the device SN used in the examination. That is, the HTTP request requesting the examination data does not include the patient personal information such as the patient ID.

Based on the device SN included in the request, the server apparatus 2 that has received the HTTP request requesting the examination data determines the order information 1303 in which the device SN is "1000" and the status information is "under examination" in the examination order storage area 13 (step S122*b*). After that, by using the patient ID in the order information 1303, out of the examination data associated with the patient ID called "aaaaaaaa" in the examination information storage area 11, the server apparatus 2 reads the examination data on the examination currently performed, and transmits the examination data as examination information to the first user terminal 301 (steps S122*c* and S123). Upon receiving the examination information, the first user terminal 301 displays, for example, an examination information screen 18 as illustrated in FIG. 11 on the display panel 15 (step S124). The examination information screen 18 includes, for example, a display field 1801 displaying the examination data acquired by the first examination device 401 and an input field 1802 to input findings about the examination data. Note that the examination data requested by the first user terminal 301 by the HTTP request is not limited to the examination data on the examination currently performed, but may be the examination data on the examination performed in the past. When the examination data on the examination performed in the past is requested, for example, the date when the examination is performed is designated in the URL of the HTTP request. When the examination data on the examination performed in the past is requested, the display panel 15 of the first user terminal 301 displays a screen similar to the examination information screen 18 illustrated in FIG. 11 and in which the examination date is the date designated by the HTTP request.

In the above description, a combination of the first examination device 401 and the first user terminal 301 is described, but similar processing can be performed in a combination of the second examination device 402 and the second user terminal 302 in the in-hospital network 1 illustrated in FIG. 1, and in a combination of another examination device 4 and user terminal 3 that are not shown.

In this way, in the in-hospital network 1 of the present embodiment, by transmitting the request command using HTTP, which is a general-purpose protocol, from the user terminal 3 to the server apparatus 2, the patient examination data can be read without installing a dedicated application in the user terminal 3. Moreover, when the examination data to be read is designated by the URL of the HTTP request, instead of the patient identification information for identifying the patient, the device identification information for identifying the examination device used for the examination on the patient is used to determine the examination data to be read based on the correspondence between the patient identification information and the device identification information managed by the server apparatus 2. Therefore, the in-hospital network 1 of the present embodiment can prevent the patient personal information from leaking from the request command using a general-purpose protocol and transmitted from the user terminal 3 to the server apparatus 2 via the transmission channel 5.

Note that the HTTP request to be transmitted from the user terminal 3 to the server apparatus 2 in the in-hospital network 1 according to the present embodiment is not limited to the examination distribution instruction described above or the request command requesting the examination data on the patient under examination, but may be a request command requesting another information. For example, the HTTP request may be a request command requesting the patient information on the patient for whom the examination distribution is performed, or a request command requesting the examination data (examination history) on the examination the patient for whom the examination distribution is performed has undergone in the past. These request commands (HTTP requests) may be transmitted from the user terminal 3 to the server apparatus 2 before the examination is started on the target patient.

Figure 12:
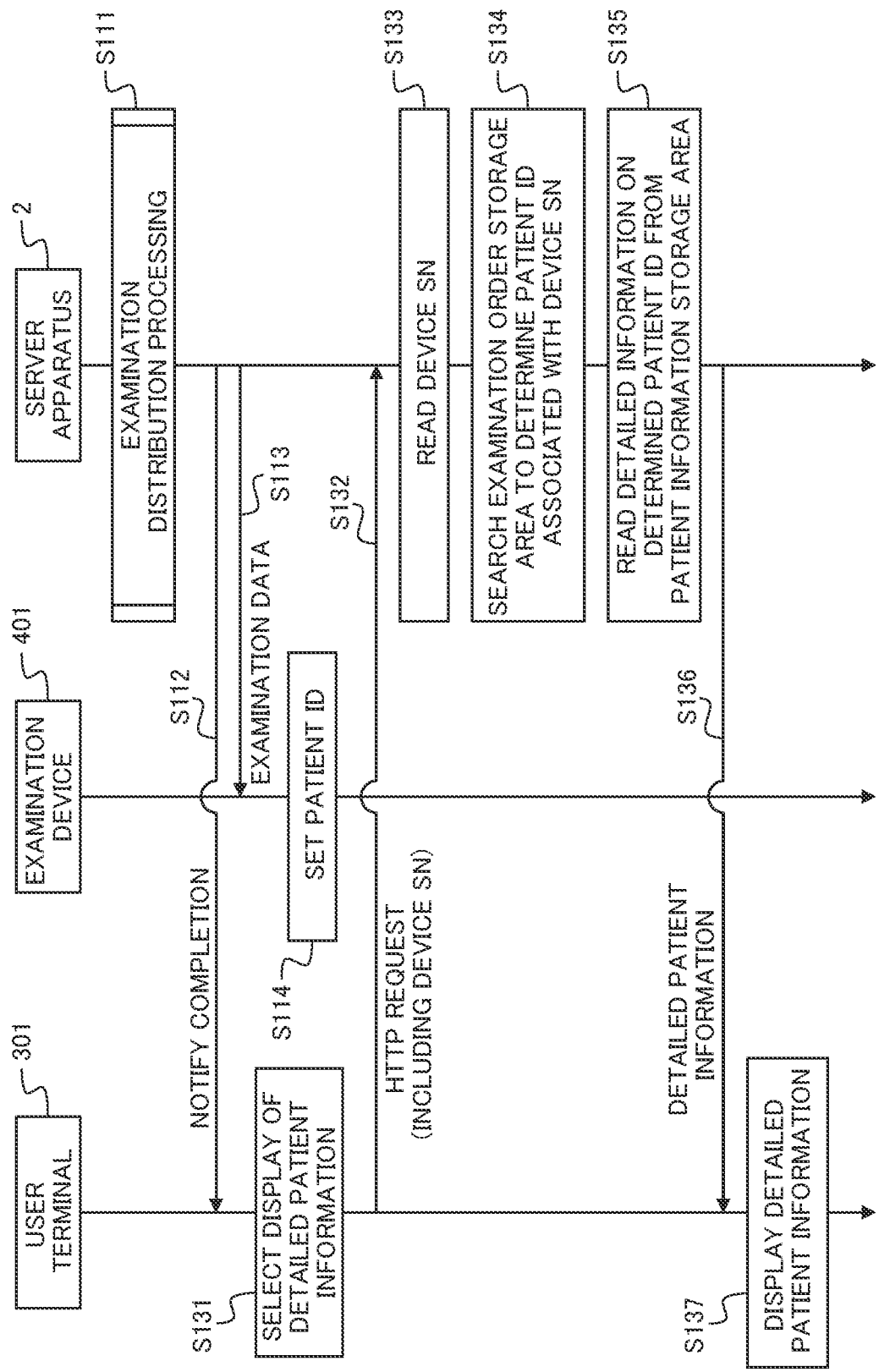
FIG. 12 is sequence diagram for describing one example of processing of reading the patient information to be performed in the in-hospital network according to one embodiment.

FIG. 12 is sequence diagram for describing one example of processing of reading the patient information to be performed in the in-hospital network according to one embodiment. FIG. 12 shows one example of processing to be performed by the first examination device 401, the first user terminal 301, and the server apparatus 2 when the patient information on the patient who undergoes the examination using the first examination device 401 is read by using the first user terminal 301 associated with the first examination device 401. FIG. 12 also shows one example of processing to be performed by the first examination device 401, the first user terminal 301, and the server apparatus 2 after the pre-examination preparation including the examination distribution processing (step S111) in the sequence diagram of FIG. 3 is performed. The examination distribution processing (step S111) includes, for example, processing such as steps S111a to S111d illustrated in FIG. 5.

When the pre-examination preparation including the examination distribution processing (for example, processing of steps S105 to S114 illustrated in FIG. 3) is finished, the user of the first user terminal 301 (doctor 701) can, for example, operate the first user terminal 301 to return the display of the display panel 15 to the menu screen. The doctor 701 can, for example, operate the first user terminal 301 to select display of the detailed patient information from among a plurality of items displayed on the menu screen (step S131). When the display of the detailed patient information is selected, the first user terminal 301 transmits the HTTP request requesting the detailed patient information to the server apparatus 2 (step S132). The HTTP request to be transmitted to the server apparatus 2 in step S132 designates the target of the request by the URL including the parameter indicating that the detailed patient information is requested, and the parameter indicating the device identification information (device SN) for identifying the first examination device 401 used for the examination on the patient. That is, in a similar manner to the HTTP request requesting the examination information under examination described above, the HTTP request to be transmitted to the server apparatus 2 in step S132 designates the target of the request by the URL that does not include the patient identification information for identifying the patient.

The server apparatus 2 that has received the HTTP request reads the device SN from the URL of the request (step S133). Subsequently, in the server apparatus 2, the determination unit 220 searches the examination order storage area 13 to determine the patient ID from the order information including the read device SN (step S134). After that, the server apparatus 2 reads the patient information including the patient ID determined in step S134, out of the patient information in the patient information storage area 10 (step S135), and transmits the read patient information as detailed patient information to the first user terminal 301 (step S136). Upon receiving the detailed patient information, the first user terminal 301 displays the detailed patient information on the display panel 15 (step S137).

Figure 13:
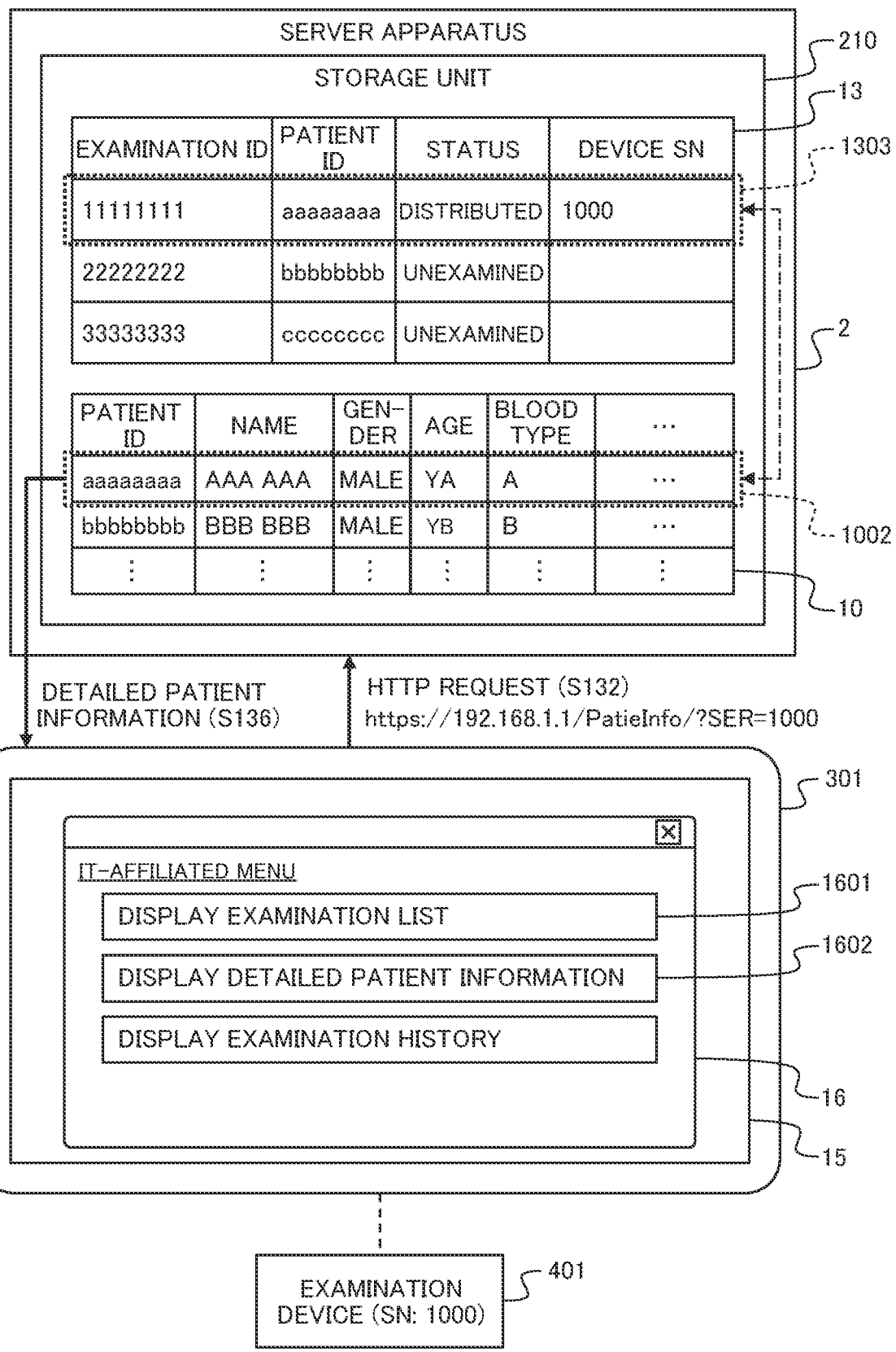
FIG. 13 is a diagram for describing a specific example of processing of displaying detailed patient information on the first user terminal.
Figure 14:
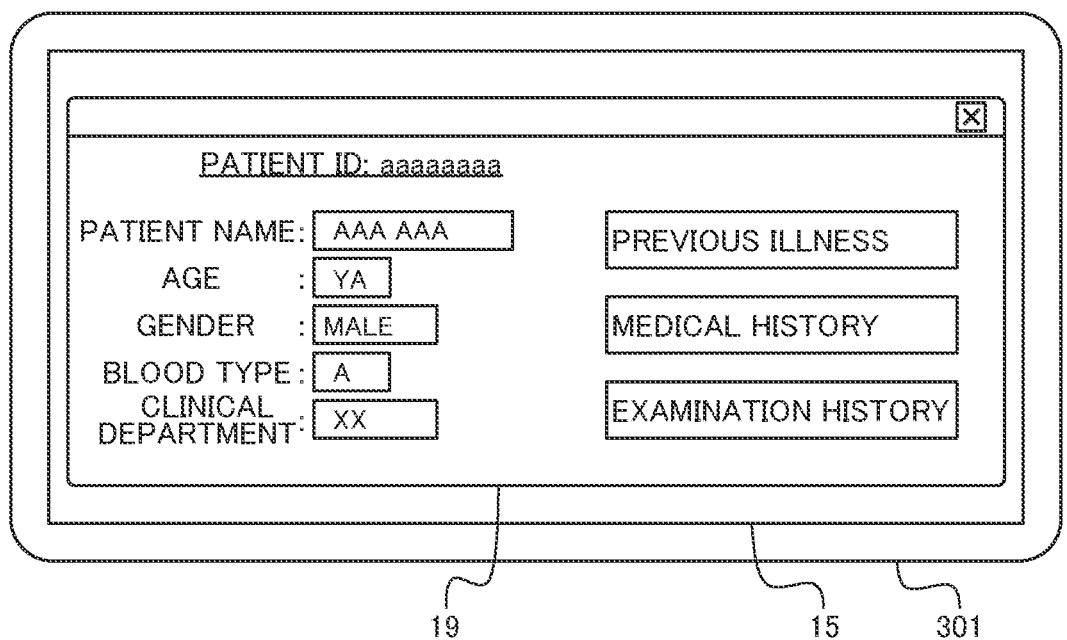
FIG. 14 is a diagram for describing one example of the detailed patient information to be displayed on the first user terminal.

FIG. 13 is a diagram for describing a specific example of processing of displaying the detailed patient information on the first user terminal. FIG. 14 is a diagram for describing one example of the detailed patient information to be displayed on the first user terminal. Note that in FIGS. 13 and 14, the reception unit 201, the transmission unit 202, and the determination unit 220 of the server apparatus 2 are omitted.

The menu screen 16 including the button 1601 of the "display examination list" described above is displayed on the display panel 15 of the first user terminal 301 illustrated in FIG. 13. After performing the examination distribution processing described above (step S111), when a button 1602 of "display detailed patient information" provided in the menu screen 16 is pressed, the first user terminal 301 transmits the HTTP request requesting the detailed patient information to the server apparatus 2 (step S132). This HTTP request includes, for example, the URL (https://192.168.1.1/PatieInfo/?SER=1000) as illustrated in FIG. 13. In this URL, "PatieInfo/" is a parameter indicating the detailed patient information, and "?SER=1000" is a parameter indicating the device identification information on the examination device to be used for the examination on the patient.

Upon receiving the HTTP request requesting the detailed patient information, the server apparatus 2 reads the device identification information (device SN) described in the URL of the request, and determines the order information 1303 including the read device SN in the examination order storage area 13 (step S134). After that, based on the patient ID in the determined order information 1303, the server apparatus 2 reads the patient information 1002 in the patient information storage area 10 (step S135), and transmits the patient information 1002 to the first user terminal 301 (step S136). Upon receiving the detailed patient information (patient information 1002), the first user terminal 301 displays, for example, a patient information display screen 19 as illustrated in FIG. 14 on the display panel 15. Note that the patient information display screen 19 illustrated in FIG. 14 is merely one example of the screen displaying the detailed patient information. The screen for displaying the detailed patient information can be appropriately changed according to the type of detailed information to be displayed and the like. For example, the detailed patient information to be displayed on the display panel 15 of the first user terminal 301 may include a medicine used and precautions when the examination peculiar to the patient is performed (for example, information indicating a part recognized as requiring follow-up in the past examination, and the like), and the like.

In this way, in the in-hospital network 1 of the present embodiment, it is possible to request the detailed patient information from the first user terminal 301 to the server apparatus 2 by the HTTP request that does not include the patient personal information, and the patient personal information will not be leaked from the HTTP request. Since the detailed patient information can be read by using the first user terminal 301 before starting the examination, it is possible to confirm the patient who will undergo the examination in advance, to confirm the points to be noted during the examination, and the like.

In the above description, a combination of the first examination device 401 and the first user terminal 301 is described, but similar processing can be performed in a combination of the second examination device 402 and the second user terminal 302 in the in-hospital network 1 illustrated in FIG. 1, and in a combination of another examination device 4 and user terminal 3 that are not shown.

Figure 15:
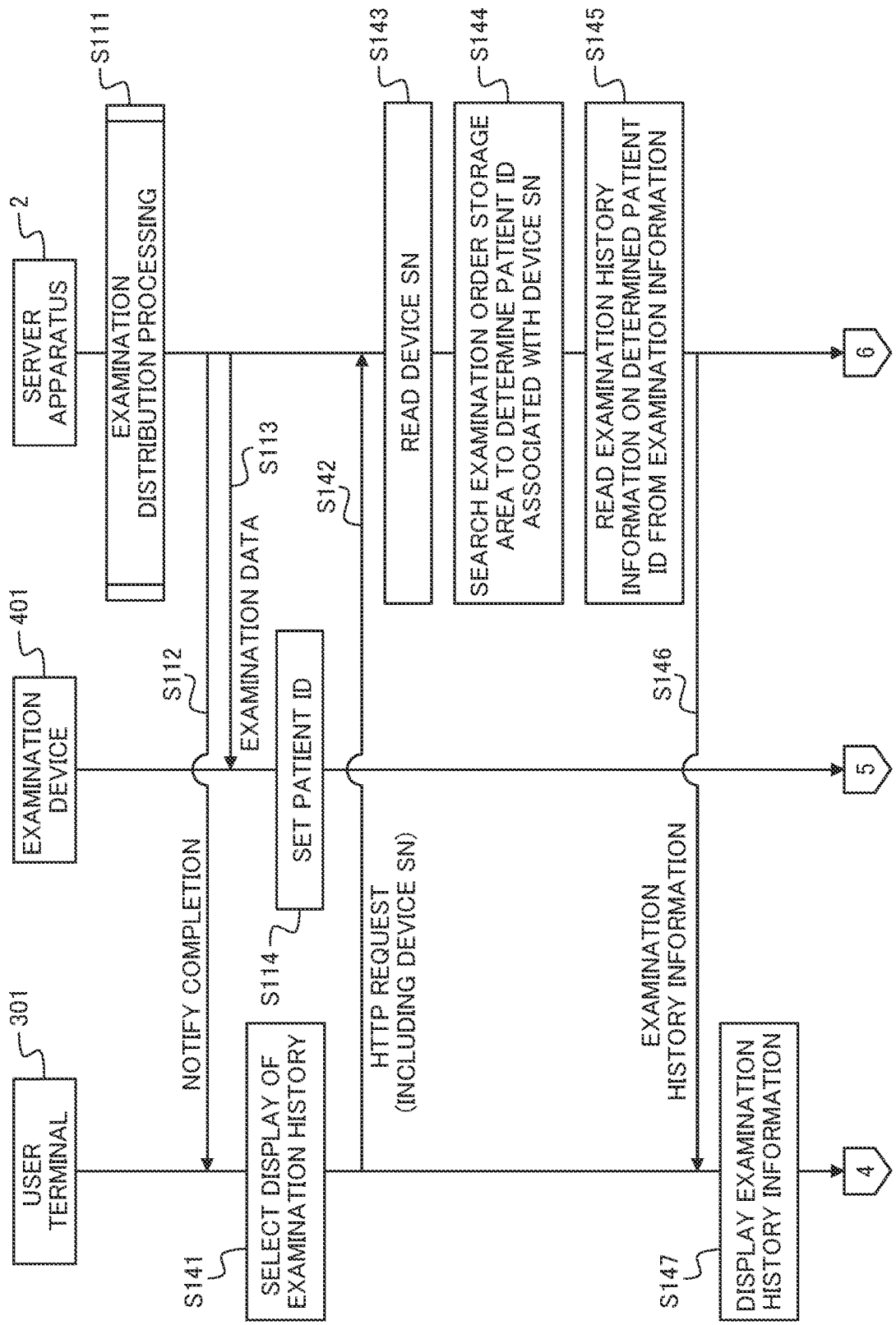
FIG. 15 is a sequence diagram (No. 1) for describing one example of processing of reading an examination history to be performed in the in-hospital network according to one embodiment.
Figure 16:
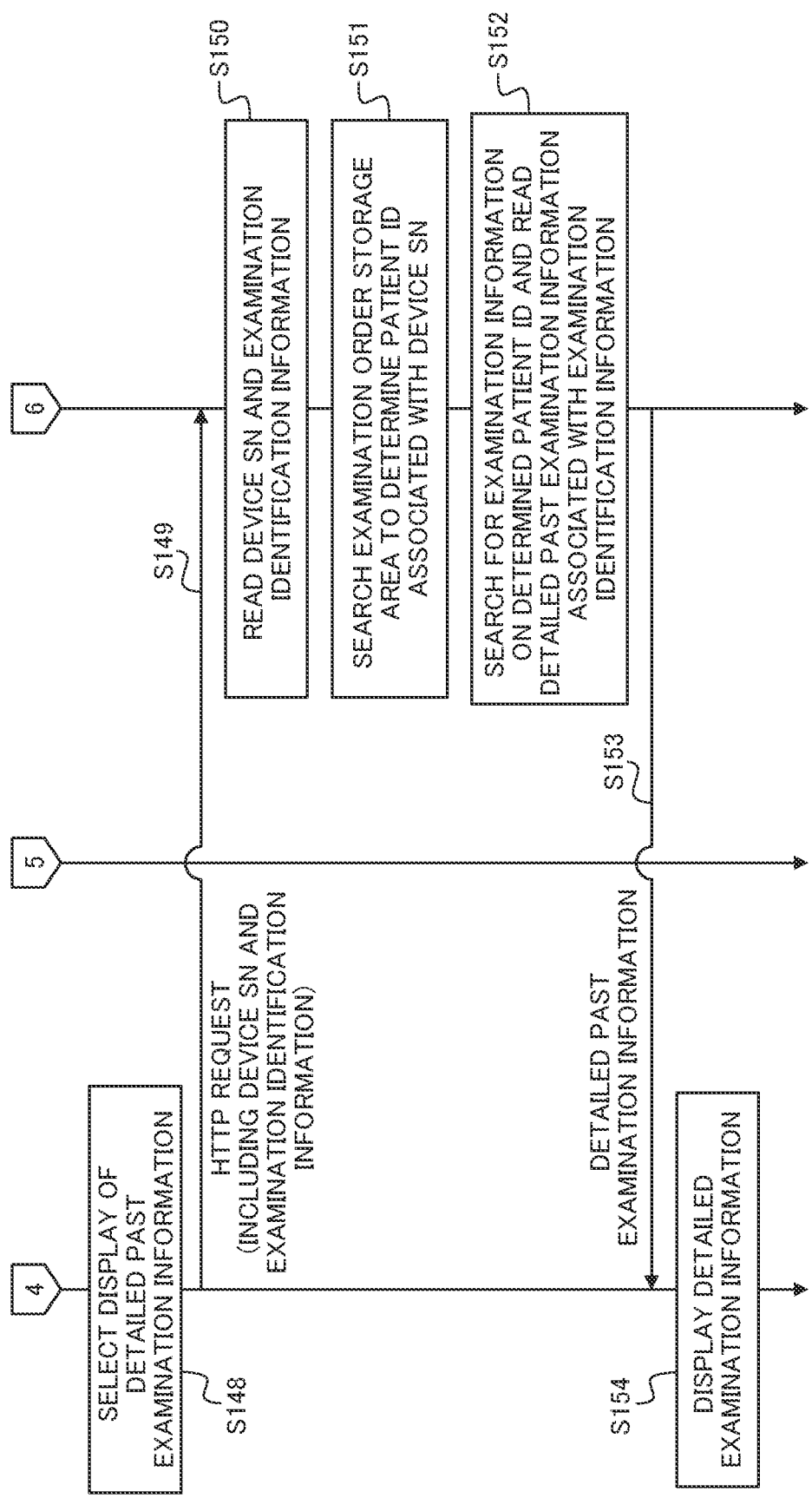
FIG. 16 is a sequence diagram (No. 2) for describing one example of processing of reading the examination history to be performed in the in-hospital network according to one embodiment.

FIG. 15 is a sequence diagram (No. 1) for describing one example of processing of reading the examination history to be performed in the in-hospital network according to one embodiment. FIG. 16 is a sequence diagram (No. 2) for describing one example of processing of reading the examination history to be performed in the in-hospital network according to one embodiment. FIGS. 15 and 16 show one example of processing to be performed by the first examination device 401, the first user terminal 301, and the server apparatus 2 when the examination history on the patient who undergoes the examination using the first examination device 401 is read by using the first user terminal 301 associated with the first examination device 401. FIGS. 15 and 16 also show one example of processing to be performed by the first examination device 401, the first user terminal 301, and the server apparatus 2 after the pre-examination preparation including the examination distribution processing (step S111) in the sequence diagram of FIG. 3 is performed. The examination distribution processing (step S111) includes, for example, processing such as steps S111a to S111d illustrated in FIG. 5.

When the pre-examination preparation including the examination distribution processing (for example, processing of steps S105 to S114 illustrated in FIG. 3) is finished, the user of the first user terminal 301 (doctor 701) can, for example, operate the first user terminal 301 to return the display of the display panel 15 to the menu screen. The doctor 701 can, for example, operate the first user terminal 301 to select display of the examination history of the patient from among a plurality of items displayed on the menu screen (step S141). When display of the examination history of the patient is selected, the first user terminal 301 transmits the HTTP request requesting the examination history of the patient to the server apparatus 2 (step S142). The HTTP request to be transmitted to the server apparatus 2 in step S142 designates the target of the request by the URL including the parameter indicating that the examination history of the patient is requested, and the parameter indicating the device identification information (device SN) for identifying the first examination device 401 used for the examination on the patient. That is, in a similar manner to the HTTP request requesting the above-described examination information under examination, the patient information, and the like, the HTTP request to be transmitted to the server apparatus 2 in step S142 designates the target of the request by the URL that does not include the patient identification information for identifying the patient.

The server apparatus 2 that has received the HTTP request reads the device SN from the URL of the request (step S143). Subsequently, in the server apparatus 2, the determination unit 220 searches the examination order storage area 13 to determine the patient ID from the order information including the read device SN (step S144). After that, the server apparatus 2 reads the examination history information associated with the patient ID determined in step S144 out of the examination information in the examination information storage area 11 (step S145), and transmits the read examination history information to the first user terminal 301 (step S146). Here, the examination history information is information indicating the examination the patient has undergone in the past and includes, for example, information indicating the examination date and the examination type, out of the examination information in the examination information storage area 11 illustrated in FIG. 2. Upon receiving the examination history information, the first user terminal 301 displays the examination history information on the display panel 15 (step S147).

After the examination history information is displayed on the first user terminal 301, the doctor 701 can select, for example, display of the detailed past examination information as shown in FIG. 16 (step S148). Here, the detailed past examination information is detailed information on the examination the patient presented by the examination history has undergone in the past (for example, examination data such as images and doctor's findings based on the examination data).

When display of the detailed past examination information is selected, the first user terminal 301 transmits the HTTP request requesting the detailed past examination information to the server apparatus 2 (step S149). The HTTP request to be transmitted to the server apparatus 2 in step S149 designates the target of the request by the URL including the parameter indicating that the detailed past examination information is requested, the parameter indicating the device identification information (device SN) for identifying the first examination device 401 used for the examination on the patient, and the parameter indicating the examination identification information for identifying the examination requesting the detailed information. The examination identification information is, for example, the examination date. That is, in a similar manner to the HTTP request requesting the examination information under examination described above, the HTTP request to be transmitted to the server apparatus 2 in step S149 designates the target of the request by the URL that does not include the patient identification information for identifying the patient.

The server apparatus 2 that has received the HTTP request reads the device SN and the examination identification information (examination date) from the URL of the request (step S150). Subsequently, in the server apparatus 2, the determination unit 220 searches the examination order storage area 13 to determine the patient ID from the order information including the read device SN (step S151). After that, the server apparatus 2 searches the examination information in the examination information storage area 11 for the examination information including the patient ID determined in step S151, and reads the detailed past examination information associated with the examination identification information (examination date) (step S152). In step S152, the server apparatus 2 reads, for example, information such as the examination data associated with the examination identification information (for example, image data) and findings of the doctor 701 based on the examination data. The server apparatus 2 transmits the read detailed past examination information to the first user terminal 301 (step S153). Upon receiving the detailed past examination information, the first user terminal 301 displays the detailed past examination information on the display panel 15 (step S154).

Figure 17:
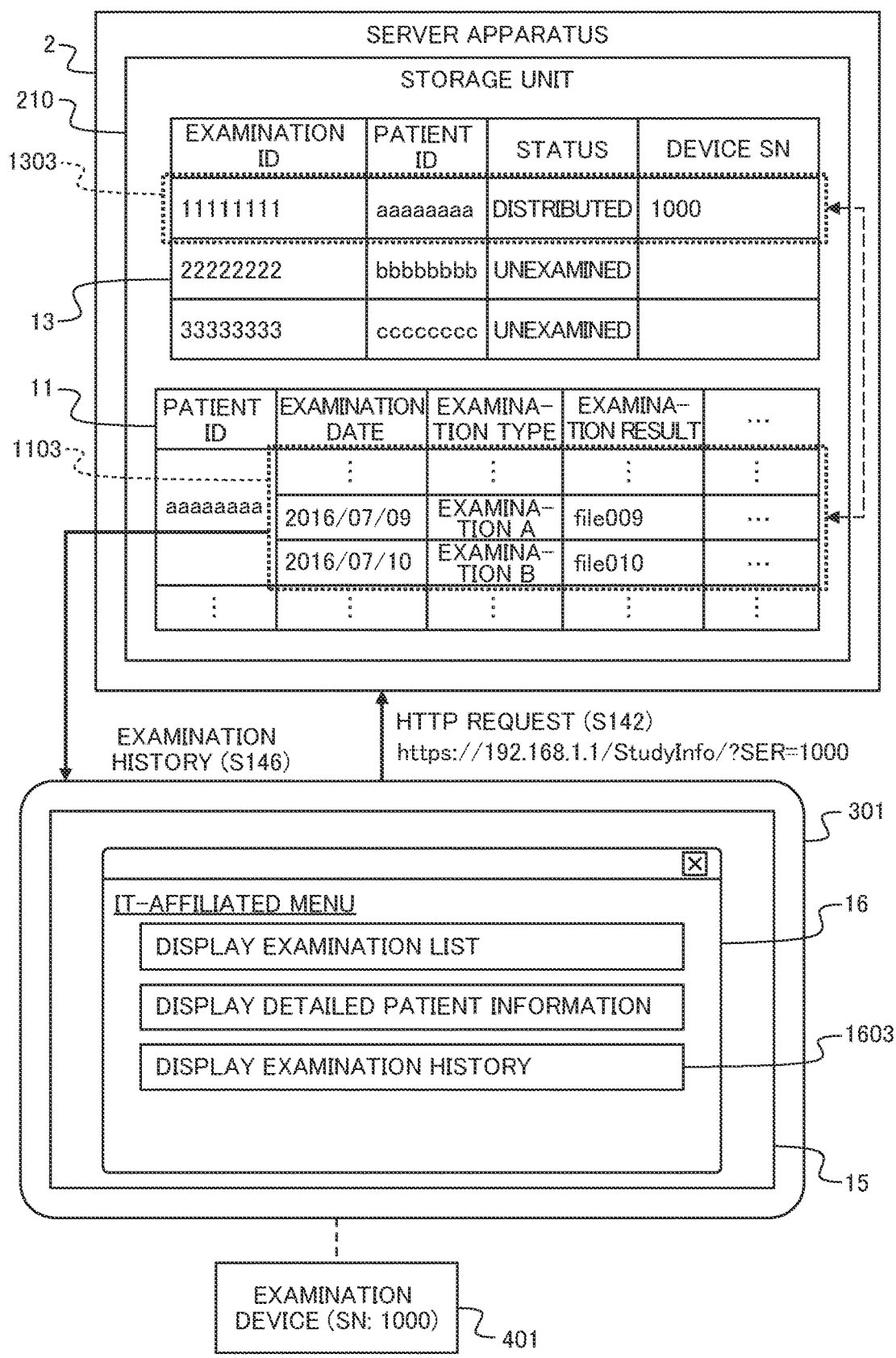
FIG. 17 is a diagram for describing a specific example of processing of displaying examination history information on the first user terminal.
Figure 18:
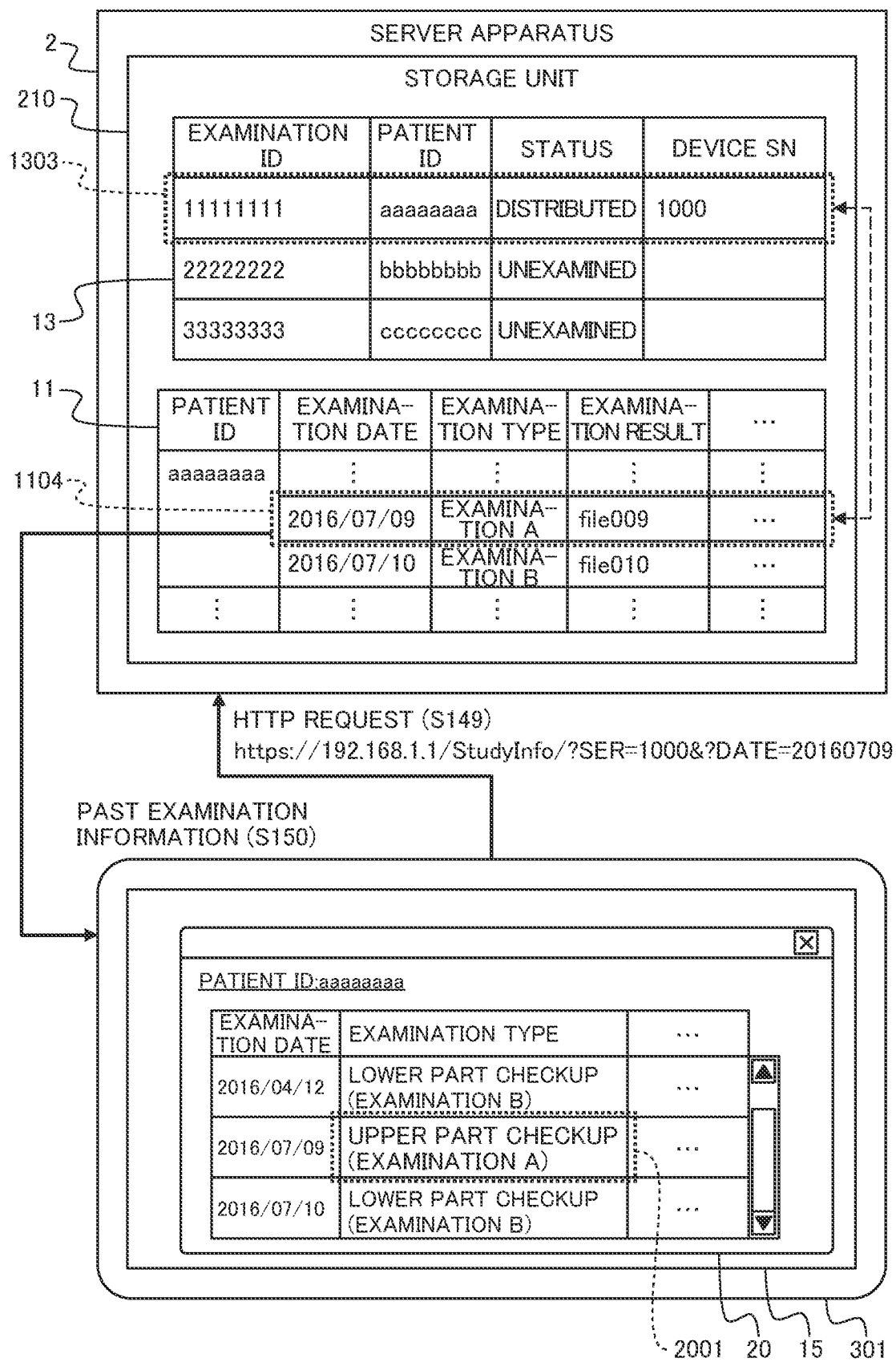
FIG. 18 is a diagram for describing a specific example of processing of displaying detailed past examination information on the first user terminal.

FIG. 17 is a diagram for describing a specific example of processing of displaying examination history information on the first user terminal. FIG. 18 is a diagram for describing a specific example of processing of displaying the detailed past examination information on the first user terminal. Note that in FIGS. 17 and 18, the reception unit 201, the transmission unit 202, and the determination unit 220 of the server apparatus 2 are omitted.

The above-described menu screen 16 is displayed on the display panel 15 of the first user terminal 301 illustrated in FIG. 17. After performing the examination distribution processing described above (step S111), when a button 1603 of "display examination history" provided in the menu screen 16 is pressed, the first user terminal 301 transmits the HTTP request requesting the examination history information to the server apparatus 2 (step S142). This HTTP request includes, for example, the URL (https://192.168.1.1/StudyInfo/?SER=1000) as illustrated in FIG. 17. In this URL, "StudyInfo/" is a parameter indicating the examination history information, and "?SER=1000" is a parameter indicating the device identification information on the examination device to be used for the examination on the patient.

Upon receiving the HTTP request requesting the examination history information, the server apparatus 2 reads the device identification information (device SN) described in the URL of the request, and determines the order information 1303 including the read device SN from the order information in the examination order storage area (step S144). After that, out of the patient information in the examination information storage area 11, from examination information 1103 associated with the patient ID in the order information 1303 determined in step S144, the server apparatus 2 reads the examination history information (for example, examination date and examination type) (step S145), and transmits the examination history information to the first user terminal 301 (step S146). Upon receiving the examination history information, the first user terminal 301 displays, for example, the examination history display screen 20 including the examination date and the examination type of the examination the patient whose patient ID is "aaaaaaaa" has undergone in the past on the display panel 15 as illustrated in FIG. 18.

When the examination history display screen 20 is displayed on the first user terminal 301, the user of the first user terminal 301 (doctor 701) can select the examination included in the examination history display screen 20 and read the detailed information on the selected examination. For example, when a field 2001 of "upper part checkup (examination A)" in the examination history display screen 20 illustrated in FIG. 18 is selected by a method such as pressing, the first user terminal 301 transmits the HTTP request requesting detailed information on the selected the examination (detailed past examination information) to the server apparatus 2 (step S149). This HTTP request includes, for example, the URL (https://192.168.1.1/StudyInfo/?SER=1000&?DATE=20160709) as illustrated in FIG. 18. In this URL, "?SER=1000" is a parameter indicating the device identification information on the examination device used for the examination on the patient, and "?DATE=20160709" is a parameter indicating the examination date of the examination requesting detailed information (examination identification information).

Upon receiving the HTTP request requesting the detailed past examination information, the server apparatus 2 reads the device identification information (device SN) and the examination identification information (examination date) described in the URL of the request (step S150). Subsequently, the server apparatus 2 determines the order information 1303 including the read device SN in the examination order storage area 13 (step S151). After that, the server apparatus 2 reads examination information 1104 on the examination date read in step S150, the examination information being associated with the patient ID in the order information 1303 determined in step S151, out of the examination information in the examination information storage area 11 (step S152). The server apparatus 2 transmits the examination information 1104 read in step S152 to the first user terminal 301 as detailed past examination information (step S153). Upon receiving the detailed past examination information (examination information 1104), the first user terminal 301 displays, on the display panel 15, for example, the examination information screen similar to the examination information screen 18 illustrated in FIG. 11 and in which the date designated by the HTTP request is displayed in the examination date field.

In this way, in the in-hospital network 1 of the present embodiment, it is possible to request the past examination result of the patient from the first user terminal 301 to the server apparatus 2 by the HTTP request that does not include the patient personal information, and the patient personal information will not be leaked from the HTTP request. Since the past examination result of the patient can be read by using the first user terminal 301 before starting the examination, it is possible to check points to note in the examination this time, for example, the existence of parts and examination items that need to be examined in detail, and to consider in advance how to proceed with the examination.

Note that when the detailed information on the past examination described above is read with the first user terminal 301, the examination to be read may be able to be designated from a screen different from the menu screen 16 illustrated in FIG. 17 and the examination history display screen 20 illustrated in FIG. 18.

In the above description, a combination of the first examination device 401 and the first user terminal 301 is described, but similar processing can be performed in a combination of the second examination device 402 and the second user terminal 302 in the in-hospital network 1 illustrated in FIG. 1, and in a combination of another examination device 4 and user terminal 3 that are not shown.

In the in-hospital network 1 according to the present embodiment, the patient can be determined by the determination unit 220 of the server apparatus 2, based on the correspondence of the device identification information for identifying the examination device used for the examination on the patient, the patient identification information housed in the examination order storage area 13 in the storage unit 210 of the server apparatus 2, the device identification information, and the status information. Therefore, in the in-hospital network 1, when information on the patient is read by using the user terminal 3, the request command that does not include the patient personal information such as the patient ID can be transmitted from the user terminal 3 to the server apparatus 2, and information according to the request command can be displayed on the user terminal 3. A plurality of patients undergoes the examination using one examination device (for example, first examination device 401) within a predetermined period (for example, one day) in many cases. Therefore, even if the device identification information leaks from the request command including the device identification information, it is difficult to determine the patient from the device identification information. Therefore, even if the request command transmitted from the user terminal 3 to the server apparatus 2 is a request command using a general-purpose protocol (for example, HTTP request), it is possible to prevent the leakage of patient personal information.

The server apparatus 2 in the in-hospital network 1 described above is implemented, for example, by a computer and a program that causes the computer to perform the processing shown in FIGS. 5, 6, 12, 15, and 16.

Figure 19:
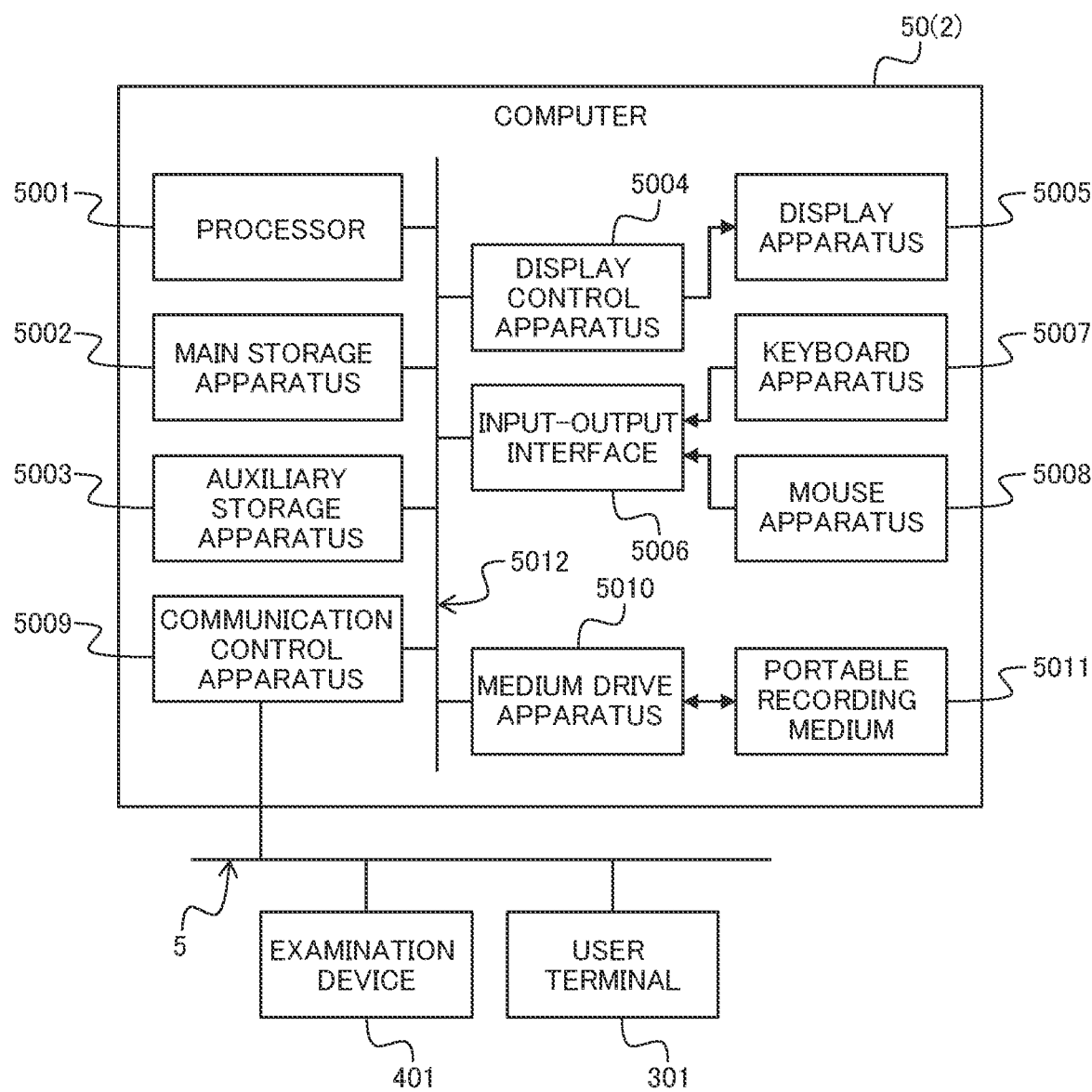
FIG. 19 is a diagram for describing a hardware configuration example of a computer.

FIG. 19 is a diagram for describing a hardware configuration example of a computer.

A computer 50 illustrated in FIG. 19 includes a processor 5001, a main storage apparatus 5002, an auxiliary storage apparatus 5003, a display control apparatus 5004, a display apparatus 5005, an input-output interface 5006, a keyboard apparatus 5007, a mouse apparatus 5008, a communication control apparatus 5009, and a medium drive apparatus 5010. The processor 5001, the main storage apparatus 5002, the auxiliary storage apparatus 5003, the display control apparatus 5004, the input-output interface 5006, the communication control apparatus 5009, and the medium drive apparatus 5010 can transmit and receive data to and from each other via a bus 5012.

The processor 5001 controls the operation of the computer 50 to function as the server apparatus 2 described above by executing an operating system (OS) or a program including the processes shown in FIGS. 5, 6, 12, 15, and 16. The processor 5001 includes, for example, one or more central processing units (CPUs). The processor 5001 may include, for example, a digital signal processor (DSP). The processor 5001 to execute the program including the processes shown in FIGS. 5, 6, 12, 15, and 16 is one example of hardware that implements functions of the determination unit 220 of the server apparatus 2 described above.

The main storage apparatus 5002 includes a read only memory (ROM) and a random access memory (RAM). The auxiliary storage apparatus 5003 is, for example, a storage apparatus having a larger storage capacity than the main storage apparatus 5002, such as a hard disk drive (HDD) or a solid state drive (SSD). The main storage apparatus 5002 and the auxiliary storage apparatus 5003 provide a storage area for storing (housing) programs to be executed by the processor 5001 and various data to be used when the processor 5001 executes the programs. For example, the auxiliary storage apparatus 5003 is one example of hardware that implements functions of the storage unit 210 of the server apparatus 2, and provides one or more of the patient information storage area 10, the examination information storage area 11, the device information storage area 12, and the examination order storage area 13 described above.

The display control apparatus 5004 controls display of the display apparatus 5005 such as a liquid crystal display. The input-output interface 5006 is a hardware interface that receives input signals from an input apparatus such as the keyboard apparatus 5007 and the mouse apparatus 5008, and outputs output signals to an output apparatus (for example, printer and the like) (not shown).

The communication control apparatus 5009 controls communication with the user terminal 3, the examination device 4, and the like via the transmission channel 5. The communication control apparatus 5009 is connected to the transmission channel 5 by wired or wireless communication. The communication control apparatus 5009 is one example of hardware that implements functions of the communication unit 200 of the server apparatus 2 (reception unit 201 and transmission unit 202).

The medium drive apparatus 5010 reads information stored in a portable recording medium 5011, writes information into the portable recording medium 5011, and the like. The portable recording medium 5011 includes, for example, an optical disk, a magnetic disk, a magneto-optical disk, and a memory card. The portable recording medium 5011 may be read only or may be writable or rewritable. The rewritable portable recording medium 5011 can be used to provide one or more of the patient information storage area 10, the examination information storage area 11, the device information storage area 12, and the examination order storage area 13 described above. The combination of the medium drive apparatus 5010 and the rewritable portable recording medium 5011 can implement functions of the storage unit 210 of the server apparatus 2. The medium drive apparatus 5010 may be connected to the bus 5012 via the input-output interface 5006.

The hardware configuration of the computer 50 illustrated in FIG. 19 is merely one example of the hardware configuration of the computer that can be used as the server apparatus 2. The computer that can be used as the server apparatus 2 may not include some of components illustrated in FIG. 19 (for example, medium drive apparatus 5010 and the like).

As described above, in the in-hospital network 1 according to the present embodiment, when information on the patient accumulated in the server apparatus 2 is read by using the user terminal 3, the information can be read by transmitting the request command that does not include the patient personal information from the user terminal 3 to the server apparatus 2. Therefore, in the in-hospital network 1 of the present embodiment, it is possible to prevent the patient personal information from leaking from the request command transmitted from the user terminal 3 to the server apparatus 2 when the information on the patient is read by using the user terminal 3. Therefore, it is possible to securely read the information on the patient with the user terminal 3 using a Web browser while avoiding the risk of personal information leakage without installing a dedicated application.

In the embodiment described above, the serial number (SN) of the examination device is mentioned as device identification information used in place of the patient personal information such as the patient ID in the HTTP request. However, the device identification information is not limited to the device serial number, but may be another information that allows identification of the examination device used for the examination on the patient. The device identification information may be, for example, information for identifying the person in charge of examination who performs the examination on the patient (for example, doctor, clinical examination technician, and the like), or information for identifying the place where the examination device is installed (for example, examination room number where the examination device is installed, and the like). The device identification information may be an identification number different from the serial number of the examination device that is set for each device to identify the plurality of examination devices installed in a medical facility.

Information used in place of the patient personal information such as the patient ID in the HTTP request may be a combination of two or more pieces of information different from the patient personal information and including the device identification information. The order information for each examination housed in the examination order storage area 13 may include a plurality of pieces of order information associated with the same device identification information (device SN). For example, the examination order storage area 13 may include a plurality of pieces of order information associated with the SN of the first examination device 401 and in which the status information is "distributed". Therefore, as information used to determine the patient in the server apparatus 2, for example, the above-described HTTP request may include the device identification information and identification information different from the device identification information and the patient personal information.

In the embodiment described above, the examination device 4 used for the examination on the patient has been mentioned as one example of the medical device in the in-hospital network 1, but the medical device in the in-hospital network 1 is not limited to this example, and may be used, for example, for a treatment different from the examination on the patient. When the medical device is used to provide a treatment different from the examination, the detailed patient information and treatment history can be determined, for example, by using the device identification information included in the URL of the HTTP request and the patient ID of the patient whose status information is "treatment is being provided" among patients who receive treatment using the medical device in information on the treatment stored in the storage unit 210 of the server apparatus 2.

Furthermore, the menu screen 16, the examination list 17, the examination information screen 18, the patient information display screen 19, and the examination history display screen 20 illustrated in the drawings referenced in the embodiment described above are each merely one example of the screen displayed on the display panel 15 of the first user terminal 301 (user terminal 3). Information included in the screen displayed on the user terminal 3 by the above processing can be changed as appropriate according to, for example, the type of medical device such as the examination device 4 used in combination with the user terminal 3, the type of information transmitted to the user terminal 3 as a response to the request command such as the HTTP request, and the like. The display format and layout of various pieces of information on the screen displayed on the user terminal 3 can be changed as appropriate.

The present description is not limited to the above-described embodiment as it is, and can be embodied by modifying components without departing from the gist at the implementation stage. Various inventions can be formed by an appropriate combination of a plurality of components disclosed in the above embodiment. For example, all the components shown in the embodiment may be combined as appropriate. Furthermore, components in different embodiments may be combined as appropriate. It goes without saying that various modifications and applications can be made without departing from the spirit of the present disclosure.

What is claimed is:

1. A server apparatus comprising:
   a memory including:
     a first storage area configured to store, in association with each other:
       (i) patient information; and
       (ii) first patient identification; and
     a second storage area configured to store, in association with each other:
       (iii) medical device identification information;
       (iv) second patient identification information corresponding to (ii) the first patient identification information; and
       (v) status information indicating a status of a medical procedure,
     wherein the second storage area is a separate storage area from the first storage area; and
   at least one processor configured to:
     (a) receive a request command including (iii) the medical device identification information from a user terminal without retrieving (i) the patient information and (ii) the first patient identification information;
     (b) in the second storage area, determine (iv) the second patient identification information referring to the request command received in step (a), wherein (iv) the second patient identification information is associated with:
       (iii) the medical device identification information received in step (a); and
       (v) the status information that indicates a status that the medical procedure is under an examination;
     (c) in the first storage area, determine (i) the first patient information associated with (ii) the first patient identification information based on (iv) the second patient identification information determined in step (b); and
     (d) responsive to (c), transmit (i) the patient information to the user terminal.

2. The server apparatus according to claim 1, wherein (i) the patient information includes personal information on a treatment currently performed or performed in a past that is received by a patient.

3. The server apparatus according to claim 1, wherein (i) the patient information includes information on an examination currently performed or performed in the past that is received by the patient.

4. The server apparatus according to claim 1, wherein (iii) the medical device identification information is a serial number assigned to a medical device.

5. The server apparatus according to claim 1, wherein (iii) the medical device identification information includes identification information for identifying a person that performs a medical procedure using a medical device.

6. The server apparatus according to claim 1, wherein (iii) the medical device identification information includes information for identifying a location where the medical device is installed.

7. The server apparatus according to claim 1, wherein (ii) the first patient identification information and (iv) the second patient identification information are used for identifying the patient received the medical procedure by using the medical device.

8. The server apparatus according to claim 1, wherein the medical procedure is an examination on the patient.

9. The server apparatus according to claim 1, wherein the medical procedure is a treatment on the patient.

10. The server apparatus according to claim 1, wherein the request command is a general-purpose protocol.

11. The server apparatus according to claim 10, wherein the server apparatus is configured to communicate according to a hypertext transfer protocol as the request command.

12. The server apparatus according to claim 11, wherein the request command is a uniform resource locator including (iii) the medical device identification information.

13. The server apparatus according to claim 11, wherein the uniform resource locator does not include (ii) the first patient identification information.

14. The server apparatus according to claim 1, wherein the at least one processor is configured to:
    (e) receive a notification of start the examination from the medical device,
    (f) responsive to (e), update (v) the status information from distributed to under the examination.

15. The server apparatus according to claim 14, wherein the at least one processor is configured to:
    (g) receive (iii) the medical device identification information with (vi) examination identification information from the user terminal, (vi) the examination identification information identifying the medical procedure performing to the patient by using the medical device;
    (h) responsive to (g), update (v) the status information from unexamined to distributed.

16. The server apparatus according to claim 1, wherein the at least one processor is configured to:
    (e) determine whether a medical procedure is started; and
    (f) when the medical procedure is started, store a result of the medical procedure to the first storage area.

17. The server apparatus according to claim 1, wherein the memory is configured to:
    store a first table including (i) the patient information and (ii) the first patient identification information in association with each other in the first storage area;
    store a second table including (iii) the medical device identification information, (iv) the second patient identification information, and (v) the status information in association with each other in the second storage area.

18. A network system comprising:
    a memory including a first storage area and a second storage area, the first storage area configured to store, in association with each other:
(i) patient information; and
(ii) first patient identification; and the second storage area configured to store, in association with each other:
(iii) medical device identification information;
(iv) second patient identification information corresponding to (ii) the first patient identification information; and
(v) status information indicating a status of a medical procedure,
wherein the second storage area is a separate storage area from the first storage area;

a user terminal; and
a server apparatus including a processor configured to:
(a) receive a request command including (iii) the medical device identification information from the user terminal without retrieving (i) the patient information and (ii) the first patient identification information;
(b) in the second storage area, determine (iv) the second patient identification information referring to the request command received in step (a), wherein (iv) the second patient identification information is associated with:
(iii) the medical device identification information received in step (a); and
(v) the status information that indicates a status that the medical procedure is under an examination;
(c) in the first storage area, determine (i) the first patient information associated with (ii) the first patient identification information based on (iv) the second patient identification information determined in step (b); and
(d) responsive to (c), transmit (i) the patient information to the user terminal.

* * * * *